United States Patent [19]
Ijichi et al.

[11] Patent Number: 5,948,916
[45] Date of Patent: Sep. 7, 1999

[54] ARYLTHIADIAZOLE DERIVATIVE AND ANTIVIRAL AGENT CONTAINING THE SAME

[75] Inventors: Katsushi Ijichi, Chiba; Shiro Shigeta, Fukushima; Masanori Baba, Kagoshima; Masatoshi Fujiwara; Tomoyuki Yokota, both of Fukushima; Hiromitsu Takayama; Shin-ichiro Sakai, both of Chiba; Yasuaki Hanasaki; Teruhiko Ide, both of Kanagawa; Hiroyuki Watanabe, Yamaguchi; Kimio Katsuura, Tokyo, all of Japan

[73] Assignee: Rational Drug Design Laboratories, Japan

[21] Appl. No.: 08/809,836

[22] PCT Filed: Sep. 21, 1995

[86] PCT No.: PCT/JP95/01898

§ 371 Date: Jun. 9, 1997

§ 102(e) Date: Jun. 9, 1997

[87] PCT Pub. No.: WO96/09296

PCT Pub. Date: Mar. 28, 1996

[30] Foreign Application Priority Data

Sep. 22, 1994 [JP] Japan .................................. 6-252755

[51] Int. Cl.$^6$ .................................................. C07D 285/125
[52] U.S. Cl. ............................................ 548/135; 548/138
[58] Field of Search ..................................... 548/135, 113, 548/138

[56] References Cited

FOREIGN PATENT DOCUMENTS

| 4-66506 | 2/1992 | Japan . |
| 4-182403 | 6/1992 | Japan . |
| WO 93/20814 | 4/1992 | WIPO . |

Primary Examiner—Deborah C. Lambkin
Assistant Examiner—Ebenezer Sackey
Attorney, Agent, or Firm—Howrey & Simon; Jeffrey I. Auerbach

[57] ABSTRACT

Novel arylthiadiazole derivatives and salts thereof useful for preventing and treating human viral infection and a novel virucide which contains the arylthiadiazole derivative or a salt thereof are provided. N,N-dimethyl [3-(3-(amino-2,6-dichlorophenyl)-1,2,5-thiadiazol-4-yl] carbamate or its salt, and virucide containing the same as an effective component.

9 Claims, No Drawings

ARYLTHIADIAZOLE DERIVATIVE AND ANTIVIRAL AGENT CONTAINING THE SAME

This application is a 371 of PCT/JP95/01898 filed on Sep. 21, 1995

BACKGROUND OF THE INVENTION

1. Field of the Invention

The present invention relates to arylthiadiazole derivatives and salts thereof having antiviral activity.

2. Description of the Related Art

Thiadiazoles having herbicidal activity are described in JP-A-3-193773, JP-A-4-103575, and JP-A-4-117372. Thiadiazoles useful as an agricultural fungicide are described in JP-A-4-182403, and JP-A-4-182405. On the other hand, acyclovir (antiherpetic medicine), amantadine (antiinfluenzal medicine), azidothymidine (anti-HIV medicine, HIV: human immunodeficiency virus) are known as antiviral medicines.

No medicine is effective against viral diseases at the moment, so that effective antiviral medicines are desired to be developed. In particular, development of anti-HIV medicine is urgent.

DISCLOSURE OF THE INVENTION

After comprehensive investigation, it was found by the inventors of the present invention that arylthiadiazole derivatives have excellent antiviral activity. Based on the findings, the present invention has been accomplished.

The present invention provides arylthiadiazole derivatives represented by General Formula [I], and salts thereof:

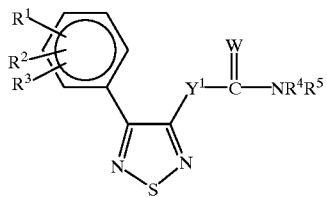

[I]

where $Y^1$ is an oxygen atom or a sulfur atom; W is an oxygen atom or a sulfur atom; one of $R^1$, $R^2$, and $R^3$ is an amino group which may be substituted by one or two independent alkyls of 1–6 carbons; a carboxyl group; a carbonyl group which is substituted by an alkoxyl of 1–4 carbons; a carbamoyl group which may be substituted by one or two independent alkyls of 1–6 carbons; a cyano group; or an alkyl group of 1–6 carbons which is substituted by a hydroxyl, an alkoxyl of 1–4 carbons, an alkoxyl of 1–4 carbons (which is further substituted by another alkoxyl of 1–4 carbons), or a silyloxy group (which is substituted by three independent alkyls of 1–6 carbons); the other two of $R^1$, $R^2$, and $R^3$ are independently a hydrogen atom; a halogen atom; an alkyl group of 1–6 carbons which may be substituted by a hydroxyl, an alkoxyl of 1–4 carbons, an alkoxyl of 1–4 carbons (which is further substituted by another alkoxyl of 1–4 carbons), or a silyloxy (which is substituted by three independent alkyls of 1–6 carbons; a trifluoromethyl group; an alkoxyl group of 1–4 carbons; a carboxyl group; a carbonyl group which is substituted by an alkoxyl of 1–4 carbons; a carbamoyl group which may be substituted by one or two independent alkyls of 1–6 carbons; a cyano group; a hydroxyl group; a hydroxymethyl group; a nitro group; or an amino group which may be substituted by one or two independent alkyls of 1–6 carbons; $R^4$, and $R^5$ are independently a hydrogen atom, an alkoxyl group of 1–4 carbons, an alkyl group of 1–6 carbons which may be substituted by an alkoxyl of 1–4 carbons, a hydroxyl, a cyano, a carboxyl, a carbamoyl, a carbonyl (substituted by alkoxyl of 1–4 carbons), or a group of

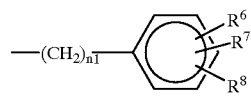

or $R^4$ and $R^5$ are linked together to form a group of

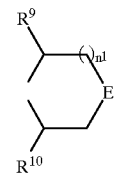

$R^6$, $R^7$, and $R^8$ are independently a hydrogen atom, a halogen atom, an alkyl group of 1–6 carbons, or an alkoxyl group of 1–4 carbons; $R^9$, and $R^{10}$ are independently a hydrogen atom, or an alkyl group of 1–6 carbons; E is a —$CH_2$— or an oxygen atom; and $n^1$ is an integer of 0 to 2.

The present invention also provides a virucide containing the arylthiadiazole derivative represented by General Formula [I] or the salt thereof as an active ingrdient.

The present invention further provides arylthiadiazole derivatives represented by the formulas below, and salts thereof:

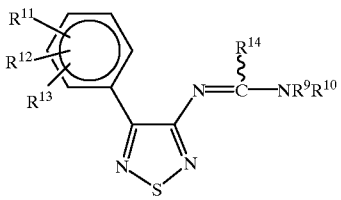

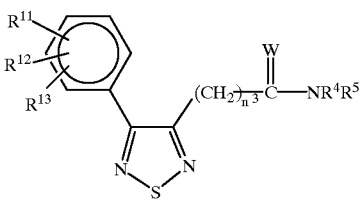

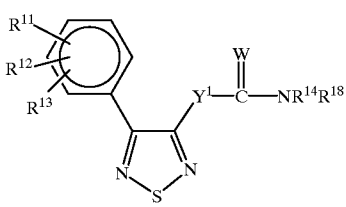

-continued

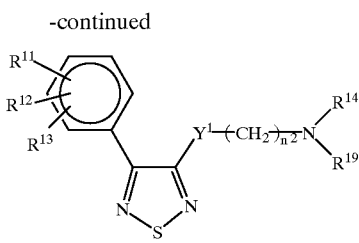

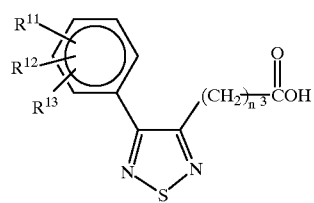

where $n^2$ is 1 or 2;

$n^3$ is 0 or 1;

$Y^1$ is an oxygen atom or a sulfur atom;

W is an oxygen atom or a sulfur atom;

$R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

$R^{14}$ is a hydrogen atom, an alkyl group of 1–6 carbons, or a phenyl group (which may be substituted by a halogen, an alkyl of 1–6 carbons, or an alkoxyl of 1–4 carbons);

$R^{18}$ is an alkyl group of 1–6 carbons which is substituted by a hydroxyl, a cyano, a carboxyl, a carbamoyl, or a carbonyl substituted by an alkoxyl group of 1–4 carbons;

$R^{19}$ is a hydrogen atom, or an alkyl group of 1–6 carbons which may be substituted by an alkoxyl of 1–4 carbons;

$R^4$, $R^5$, $R^6$, $R^7$, $R^8$, $R^9$, $R^{10}$, E, and $n^1$ are the same as mentioned above, provided that, in the last formula, $R^{11}$, $R^{12}$, and $R^{13}$ are not simultaneously a hydrogen atom when $n^3$ is 0.

The present invention further provides a virucide containing an arylthiadiazole of General Formula [II], or a salt thereof as an active ingredient:

[II]

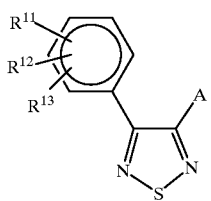

where A is a group of

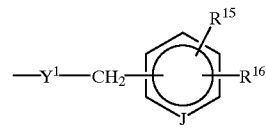

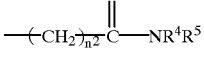

or

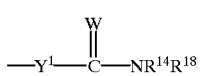

where $R^{15}$, and $R^{16}$ are independently a hydrogen atom, a halogen atom, an alkoxyl group of 1–4 carbons, a nitro group, or an alkyl group of 1–6 carbons which may be substituted with a halogen;

J is —CH=, or —N=;

$Y^2$ is an oxygen atom, a sulfur atom, or —$NR^{14}$—;

$R^{17}$ is a halogen atom, or $NR^{14}$—$R^{19}$; and $R^{11}$, $R^{12}$, $R^{13}$, $R^{14}$, $R^{18}$, $R^{19}$, $n^2$, $n^3$, $R^4$, $R^5$, $R^9$, $R^{10}$, $R^{14}$, $Y^1$, and W are the same as mentioned above.

DETAILED DESCRIPTION OF THE PREFERRED EMBODIMENT

The present invention is described in more detail.

The alkyl group of 1–6 carbons as the substituent in General Formulas [I] and [II] includes linear, branched, or cyclic alkyl groups such as methyl, ethyl, n-propyl, isopropyl, n-butyl, isobutyl, s-butyl, t-butyl, n-pentyl, cyclopentyl, n-hexyl, and cyclohexyl. The alkoxyl group of 1–4 carbons includes methoxy, ethoxy, n-propoxy, isopropoxy, n-butoxy, isobutoxy, s-butoxy, and t-butoxy. The halogen atoms includes atoms of fluorine, chlorine, bromine, and iodine.

Typical production processes are shown for the arylthiadiazole derivative represented by General Formula [I] or [II].

Production Process 1

-continued

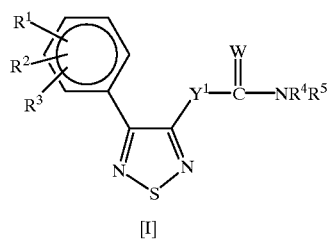

[I]

where Q is a chlorine, bromine, or iodine atom; $R^1$, $R^2$, $R^3$, $R^4$, $R^5$, $Y^1$, and W are the same as mentioned above.

The arylthiadiazole derivative represented by General Formula [I] can be produced by reaction of a derivative represented by General Formula [III] with a carbamoyl derivative represented by General Formula [IV].

The reaction is conducted in a solvent in the presence of a base at a temperature of from 0 to 150° C., preferably from 20 to 100° C., for several minutes to 24 hours, preferably from 1 to 12 hours.

The carbamoyl derivative of General Formula [IV] is used in an amount of 1–5 equivalents, preferably 1–3 equivalents, and the base is used in an amount of 1–5 equivalents, preferably 1–3 equivalents, to one equivalent of the derivative of General Formula [III].

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, and t-butanol; water, and the like.

The base includes organic bases such as pyridine, triethylamine, and N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

(Production Process 1-1)

The arylthiadiazole derivative of General Formula [I] in which at least one of $R^1$, $R^2$, and $R^3$ is an alkyl group of 1–6 carbons substituted by a hydroxyl group, and $R^4$, $R^5$, $Y^1$, and W are the same as defined above can be produced by hydrolysis of the arylthiadiazole of General Formula [I] in which at least one of $R^1$, $R^2$, and $R^3$ is an alkyl group of 1–6 carbons [which is substituted by an alkoxyl of 1–4 carbons, an alkoxyl of 1–4 carbons (which is further substituted by another alkoxyl of 1–4 carbons), or a silyloxy (which is further substituted by three independent alkyls of 1–6 carbons)], and $R^4$, $R^5$, $Y^1$, and W are the same as mentioned above.

The reaction is conducted in a solvent in the presence of an acid or a base at a temperature of from 0 to 120° C., preferably from 20 to 100° C., for several minutes to 12 hours, preferably from 1 to 6 hours.

The acid or the base is used in an amount of 1–50 equivalents, preferably 1–20 equivalents to one equivalent of the substrate substance.

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, t-butanol; water, and the like.

The base includes inorganic bases such as sodium hydroxide, potassium hydroxide, sodium carbonate, and potassium carbonate; and alkali metal alkoxides such as sodium methoxide, sodium ethoxide, potassium t-butoxide, and the like.

The acid includes protonic acids such as acetic acid, trifluoroacetic acid, hydrofluoric acid, hydrochloric acid, hydrobromic acid, and sulfuric acid; and Lewis acids such as aluminum chloride, titanium tetrachloride, boron trifluoride, boron tribromide, zinc bromide, trimethylsilyl iodide, and tetrabutylammonium fluoride.

(Production Process 1-2)

The arylthiadiazole derivative of General Formula [I] in which at least one of $R^1$, $R^2$, and $R^3$ is a carboxyl group, and $R^4$, $R^5$, $Y^1$, and W are the same as defined above can be produced by hydrolysis of the arylthiadiazole of General Formula [I] in which at least one of $R^1$, $R^2$, and $R^3$ is a carbonyl group substituted by an alkoxyl of 1–4 carbons, and $R^4$, $R^5$, $Y^1$, and W are the same as mentioned above.

The reaction is conducted in a solvent in the presence of an acid or a base at a temperature of from 0 to 120° C., preferably from 20 to 100° C., for several minutes to 12 hours, preferably from 1 to 6 hours.

The acid or the base is used in an amount of 1 to 50 equivalents, preferably 1 to 20 equivalents to one equivalent of the substrate substance.

The solvent includes ethers such as diethyl ether, tetrahydrofuran, dioxane, and dimethoxyethane; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, and t-butanol; water, and the like.

The base includes inorganic bases such as lithium hydroxide, sodium hydroxide, potassium hydroxide, sodium carbonate, and potassium carbonate; and alkali metal alkoxides such as sodium methoxide, sodium ethoxide, potassium t-butoxide, and the like.

The acid includes acetic acid, trifluoroacetic acid, hydrofluoric acid, hydrochloric acid, hydrobromic acid, sulfuric acid, trimethylsilyl chloride, boron tribromide, aluminum chloride, and the like.

(Production Process 1-3)

The arylthiadiazole derivative of General Formula [I] in which at least one of $R^1$, $R^2$, and $R^3$ is an amino group which may be substituted by one or two independent alkyls of 1–6 carbons, and $R^4$, $R^5$, $Y^1$, and W are the same as defined above can be produced by reduction, with hydrogen, of the arylthiadiazole derivative of General Formula [I] in which at least one of $R^1$, $R^2$, and $R^3$ is a nitro group, and $R^4$, $R^5$, $Y^1$, and W are the same as mentioned above in the presence of a catalyst such as platinum oxide, platinum, platinum-carbon, platinum sulfide-carbon, and palladium-carbon. Further, the amino group can be alkylated by reaction of the resulting amino group with an alkylating agent of 1–6 carbons, if necessary.

The reduction reaction is conducted in a solvent in the presence or absence of an acid at a temperature of from 0 to 80° C., preferably from 10 to 50° C., for several minutes to 24 hours, preferably from 1 to 12 hours.

The catalyst is used in an amount of 0.01 to 1 part, preferably 0.03 to 0.3 part by weight, and the acid is used in an amount of 0.1 to 10 parts, preferably 0.5 to 3 parts by weight to one part by weight of the substrate substance. The hydrogen pressure is 1 to 5 atmosphere, preferably 1 to 2 atmosphere.

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; polar solvents such as N,N-dimethylformamide, dimethylsulfoxide, 1,3-dimethyl-2-imidazolidinone, hexamethylphosphoric triamide, acetonitrile and ethyl acetate; alcohols such as methanol, ethanol, isopropanol, and t-butanol; acetic acid; water, and the like.

The catalyst includes platinum oxide, platinum, platinum-carbon, platinum sulfide-carbon, palladium-carbon, and the like.

The acid includes acetic acid, hydrochloric acid, sulfuric acid, phosphoric acid, oxalic acid, trifluoroacetic acid, and the like.

The alkylation of the resulting amino group is conducted by reaction with an alkylating agent of 1–6 carbons in a solvent in the presence or absence of a base at 0 to 130° C., preferably 20 to 100° C., for several minutes to 24 hours, preferably 1 to 12 hours.

The alkylating agent of 1–6 carbons is used in an amount of 0.5 to 5 equivalents, preferably 1 to 3 equivalents, to one equivalent of the substrate substance.

The alkylating agent includes alkyl halides, alkyl sulfate esters, and the like.

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; polar solvents such as N,N-dimethylformamide, dimethylsulfoxide, 1,3-dimethyl-2-imidazolidinone, hexamethylphosphoric triamide, acetonitrile and ethyl acetate; alcohols such as methanol, ethanol, isopropanol, and t-butanol; amines such as pyridine, triethylamine, and N,N-diisopropylethylamine; water, and the like.

The base includes organic bases such as pyridine, triethylamine, N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

Production Process 2

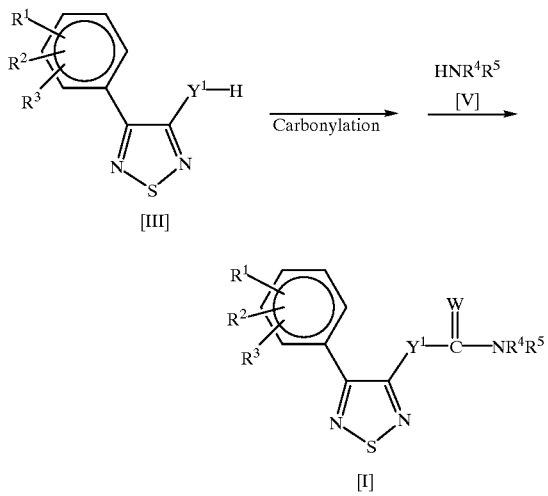

where $R^1$, $R^2$, $R^3$, $R^4$, $R^5$, $Y^1$, and W are the same as mentioned above.

The arylthiadiazole derivative represented by General Formula [I] can be produced by reaction of a derivative represented by General Formula [III] with a carbonylating agent, and subsequent reaction with an amine represented by General Formula [V].

The carbonylation is conducted in a solvent in the presence or absence of a base at 0 to 100° C., preferably 10 to 50° C., for several minutes to 24 hours, preferably 1 to 12 hours.

The carbonylating agent is used in an amount of 1 to 3 equivalents, preferably 1 to 2 equivalents, and the base is used in an amount of 1 to 5 equivalents, preferably 1 to 3 equivalents to one equivalent of the derivative represented by General Formula [III].

The carbonylating agent includes phosgene, thiophosgene, trichloromethyl chloroformate, bis(trichloromethyl) carbonate, 1,1'-thiocarbonyldiimidazole, 1,1'-carbonyldiimidazole, dimethyl carbonate, and the like.

The solvent includes hydrocarbons such as hexane, cyclohexane, benzene, toluene, and xylene; ethers such as diethyl ether, tetrahydrofuran, dioxane, and dimethoxyethane; and halogenated hydrocarbons such as dichloromethane, chloroform, carbon tetrachloride, and the like.

The base includes organic bases such as pyridine, triethylamine, N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

The subsequent reaction with the amine represented by General Formula [V] is conducted in a solvent in the presence or absence of a base at 0 to 100° C., preferably 10 to 50° C., for several minutes to 24 hours, preferably 1 to 12 hours.

The amine of General Formula [V] is used in an amount of 1 to 5 equivalents, preferably 1 to 3 equivalents, and the base is used in an amount of 1 to 5 equivalents, preferably 1 to 3 equivalents to one equivalent of the derivative represented by General Formula [III].

The solvent includes hydrocarbons such as hexane, cyclohexane, benzene, toluene, and xylene; ethers such as diethyl ether, tetrahydrofuran, dioxane, and dimethoxyethane; and halogenated hydrocarbons such as dichloromethane, chloroform, carbon tetrachloride, and the like.

The base includes organic bases such as pyridine, triethylamine, N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

Production Process 3

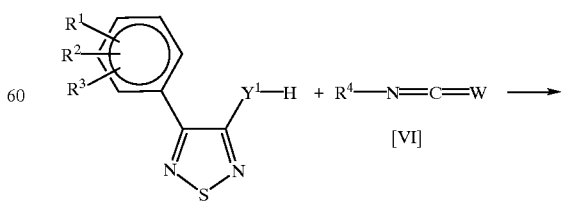

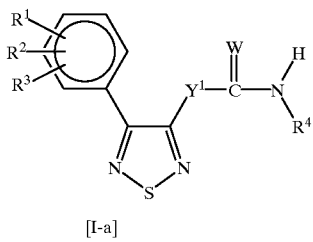

[I-a]

where $R^1$, $R^2$, $R^3$, $R^4$, $Y^1$ and W are the same as mentioned above.

The arylthiadiazole represented by General Formula [I-a] can also be produced by reaction of a derivative represented by General Formula [III] with an isocyanate represented by General Formula [VI].

The reaction is conducted in a solvent in the presence or absence of a base at 0 to 150° C., preferably 20 to 100° C., for several minutes to 24 hours, preferably 1 to 12 hours.

The isocyanate represented by General Formula [VI] is used in an amount of 1 to 30 equivalents, preferably 1 to 10 equivalents, and the base is used in an amount of 0.01 to 3 equivalents, preferably 0.01 to 1 equivalent to one equivalent of the derivative represented by General Formula [III].

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; and polar solvents such as N,N-dimethylformamide, dimethylsulfoxide, 1,3-dimethyl-2-imidazolidinone, hexamethylphosphoric triamide, acetonitrile, and the like.

The base includes organic bases such as pyridine, triethylamine, and N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

Production Process 4

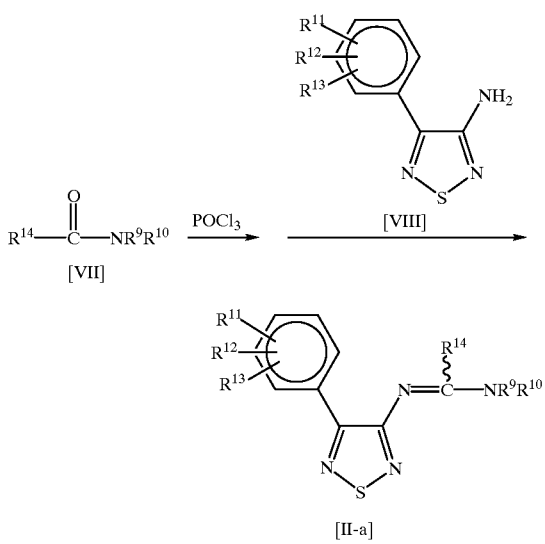

[II-a]

where $R^9$, $R^{10}$, $R^{11}$, $R^{12}$, $R^{13}$, and $R^{14}$ are the same as mentioned above.

The arylthiadiazole derivative represented by General Formula [II-a] can be produced by reaction of an amide derivative represented by General Formula [VII] with phosphorus oxychloride, and subsequent reaction with an amine derivative represented by General Formula [VIII].

The reaction with phosphorus oxychloride is conducted in a solvent at 0 to 100° C., preferably from 10 to 50° C., for several minutes to 24 hours, preferably 3 to 12 hours.

The phosphorus oxychloride is used in an amount of from 0.3 to 1.5 equivalents, preferably from 0.5 to 1.1 equivalents to one equivalent of the amide derivative represented by General Formula [VII].

The solvent includes hydrocarbons such as hexane, cyclohexane, benzene, toluene, and xylene; ethers such as diethyl ether, tetrahydrofuran, dioxane, and dimethoxyethane; and halogenated hydrocarbons such as dichloromethane, chloroform, carbon tetrachloride, and the like.

The subsequent reaction with the amine derivative represented by General Formula [VIII] is conducted in the same solvent used for the reaction with phosphorus oxychloride at 10 to 130° C., preferably 50 to 90° C., for several minutes to 12 hours, preferably 1 to 6 hours.

The amine derivative represented by General Formula [VIII] is used in an amount of 0.25 to 1 equivalent, preferably 0.5 to 1.0 equivalent to 1 equivalent of the amide derivative represented by General Formula [VII].

Production Process 5

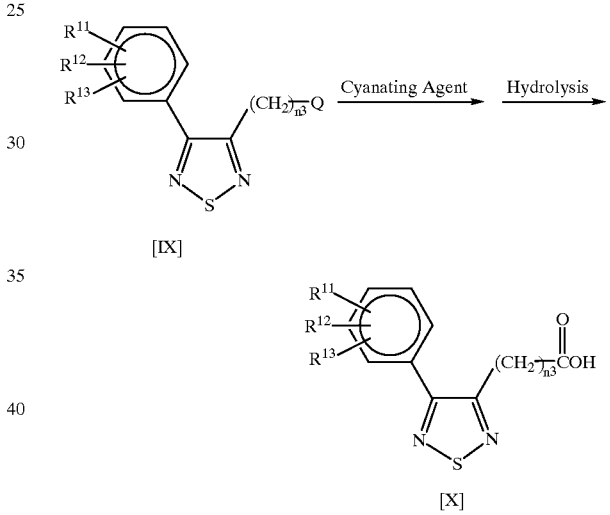

[X]

where $R^{11}$, $R^{12}$, $R^{13}$, $n^3$, and Q are the same as mentioned above.

The carboxylic acid derivative represented by General Formula [X] can be produced by reaction of a halogen compound represented by General Formula [IX] with a cyanating agent, and subsequent hydrolysis by an acid or a base.

The reaction with the cyanating agent is conducted in a solvent at 10 to 180° C., preferably 50 to 150° C., for several minutes to 24 hours, preferably 1 to 12 hours.

The cyanating agent is used in an amount of 1 to 5 equivalents, preferably 1 to 3 equivalents to one equivalent of the halogen compound represented by General Formula [IX].

The solvent includes ethers such as diethyl ether, tetrahydrofuran, dioxane, and dimethoxyethane; and polar solvents such as N,N-dimethylformamide, dimethylsulfoxide, 1,3-dimethyl-2-imidazolidinone, hexamethylphosphoric triamide, acetonitrile, and the like.

The cyanating agent includes sodium cyanide, potassium cyanide, copper cyanide, and the like.

The subsequent hydrolysis reaction is conducted in a solvent in the presence of an acid or a base at 0 to 120° C., preferably 20 to 100° C., for several minutes to 12 hours, preferably 1 to 6 hours.

The acid or the base is used in an amount of from 1 to 50 equivalents, preferably 1 to 20 equivalents, to one equivalent of the substrate substance.

The solvent includes ethers such as diethyl ether, tetrahydrofuran, dioxane, and dimethoxyethane; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, and t-butanol; water, and the like.

The base includes inorganic bases such as lithium hydroxide, sodium hydroxide, potassium hydroxide, sodium carbonate, and potassium carbonate; and alkali metal alkoxides such as sodium methoxide, sodium ethoxide, potassium t-butoxide, and the like.

The acid includes formic acid, acetic acid, trifluoroacetic acid, hydrochloric acid, hydrobromic acid, sulfuric acid, and the like.

Production Process 6

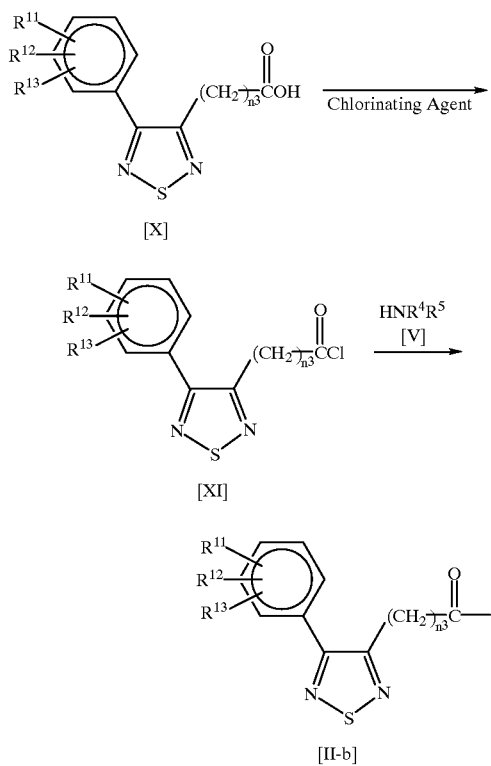

where $R^4$, $R^5$, $R^{11}$, $R^{12}$, $R^{13}$, and $n^3$ are the same as mentioned above.

The arylthiadiazole derivative represented by General Formula [II-b] can be produced by reaction of a carboxylic acid derivative represented by General Formula [X] with a chlorinating agent to form an acid chloride represented by General Formula [XI], and subsequent reaction with an amine represented by General Formula [V].

The reaction with the chlorinating agent is conducted without a solvent or in a solvent at 0 to 100° C., preferably 10 to 80° C., for several minutes to 12 hours, preferably 1 to 6 hours.

The chlorinating agent is used in an amount of 1 to 30 equivalents, preferably 1 to 10 equivalents to one equivalent of the carboxylic acid derivative represented by General Formula [X].

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; and polar solvents such as N,N-dimethylformamide, dimethylsulfoxide, 1,3-dimethyl-2-imidazolidinone, hexamethylphosphoric triamide, and the like.

The chlorinating agent includes thionyl chloride, oxalyl chloride, phosphoryl chloride, phosphorus trichloride, phosphorus pentachloride, and the like.

A brominating agent or an iodinating agent can be used in place of the chlorinating agent for the reaction.

The subsequent reaction with the amine represented by General Formula [V] is conducted in a solvent in the presence or absence of a base at 0 to 50° C., preferably 0 to 20° C., for several minutes to 6 hours, preferably 0.5 to 2 hours.

The amine represented by General Formula [V] is used in an amount of from 1 to 5 equivalents, preferably from 1 to 2 equivalents, and the base is used in an amount of from 1 to 5 equivalents, preferably 1 to 3 equivalents, to one equivalent of the acid chloride represented by General Formula [XI].

The base includes organic bases such as pyridine, triethylamine, and N,N-diisopropylethylamine; inorganic bases such as sodium hydroxide, potassium hydroxide, sodium carbonate, and potassium carbonate; and alkali metal alkoxides such as sodium methoxide, sodium ethoxide, potassium t-butoxide, and the like.

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; polar solvents such as N,N-dimethylformamide, dimethylsulfoxide, 1,3-dimethyl-2-imidazolidinone, hexamethylphosphoric triamide, and acetonitrile; water, and the like.

Production Process 7

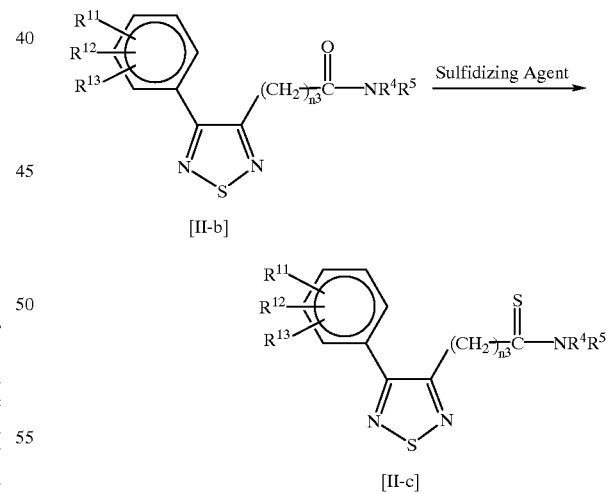

where $R^4$, $R^5$, $R^{11}$, $R^{12}$, $R_{13}$, and $n^3$ are the same as mentioned above.

The arylthiadiazole derivative represented by General Formula [II-c] can be produced by reaction of an arylthiadiazole derivative represented by General Formula [II-b] with a sulfidizing agent.

The reaction is conducted in a solvent at 20 to 150° C., preferably 50 to 100° C., for several minutes to 6 hours, preferably 0.5 to 2 hours.

The sulfidizing agent is used in an amount of 1 to 5 equivalents, preferably 1 to 2 equivalents to one equivalent of the arylthiadiazole derivative represented by General Formula [II-b].

The solvent includes hydrocarbons such as hexane, cyclohexane, benzene, toluene, and xylene; halogenated hydrocarbons such as dichloromethane, chloroform, and carbon tetrachloride; and amines such as pyridine, triethylamine, and the like.

The sulfidizing agent includes phosphorus pentasulfide, Lawesson's Reagent, and the like.

Production Process 8

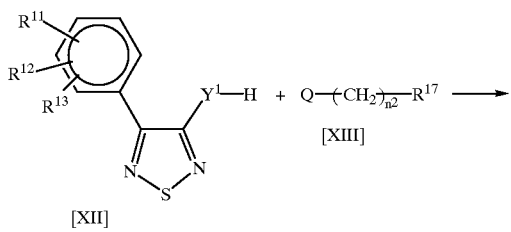

where $R^{11}$, $R^{12}$, $R^{13}$, $R^{17}$, $Y^1$, and $n^2$ are the same as mentioned above.

The arylthiadiazole derivative represented by General Formula [II-d] can be produced by reaction of a derivative represented by General Formula [XII] with a halogen compound represented by General Formula [XIII].

The reaction is conducted in a solvent in the presence of a base at 0 to 150° C., preferably 20 to 100° C., for several minutes to 24 hours, preferably 1 to 12 hours.

The halogen compound represented by General Formula [XIII] is used in an amount of 1 to 5 equivalents, preferably 1 to 3 equivalents, and the base is used in an amount of 1 to 5 equivalents, preferably 1 to 3 equivalents, to one equivalent of the derivative represented by General Formula [XII].

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, and t-butanol; water, and the like.

The base includes organic bases such as pyridine, triethylamine, and N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

Production Process 9

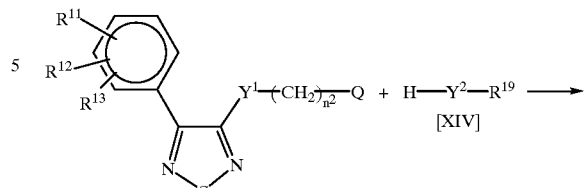

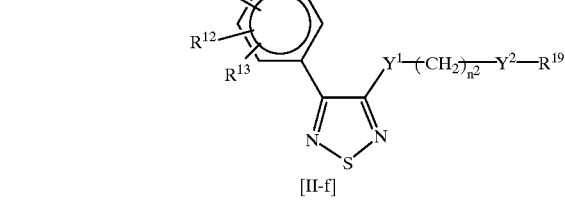

where $R^{11}$, $R^{12}$, $R^{13}$, $R^{19}$, $Y^1$, $Y^2$, $n^2$, and Q are the same as mentioned above.

The arylthiadiazole derivative represented by General Formula [II-f] can be produced by reaction of an arylthiadiazole derivative represented by General Formula [II-e] with a compound represented by General Formula [XIV].

The reaction is conducted in a solvent in the presence of a base at 0 to 150C., preferably 20 to 100° C., for several minutes to 24 hours, preferably 1 to 12 hours.

The compound represented by General Formula [XIV] is used in an amount of 1 to 5 equivalents, preferably 1 to 3 equivalents, and the base is used in an amount of 1 to 5 equivalents, preferably 1 to 3 equivalents, to one equivalent of the arylthiadiazole derivative represented by General Formula [II-e].

The solvent includes hydrocarbons such as hexane, cyclohexane, benzene, toluene, and xylene; ethers such as diethyl ether, tetrahydrofuran, dioxane, and dimethoxyethane; halogenated hydrocarbons such as dichloromethane, chloroform, and carbon tetrachloride; amines such as pyridine, and triethylamine; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, and t-butanol; water, and the like.

The base includes organic bases such as pyridine, triethylamine, and N,N-diisopropylethylamine; inorganic bases such as sodium hydroxide, potassium hydroxide, sodium carbonate, potassium carbonate, and sodium hydride; and alkali metal alkoxides such as sodium methoxide, sodium ethoxide, potassium t-butoxide, and the like.

Production Process 10

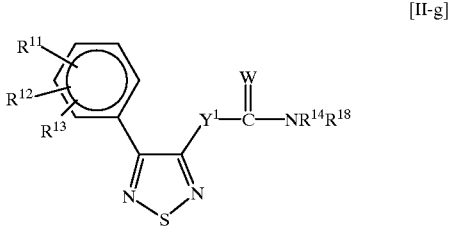

where $R^{11}$, $R^{12}$, $R^{13}$, $R^{14}$, $R^{18}$, $Y^1$, and W are the same as mentioned above. The arylthiadiazole derivative represented by General Formula [II-g] can be produced in a similar manner as in Production Process 1, 2, or 3.

15

(Production Process 10-1)

The arylthiadiazole derivative of General Formula [II-g] in which $R^{18}$ is an alkyl group of 1 to 6 carbons substituted by a carboxyl or carbamoyl group, and $R^{11}$, $R^{12}$, $R^{13}$, $R^{14}$, $Y^1$, and W are the same as mentioned above can be produced by hydrolysis of the arylthiadiazole derivative represented by General Formula [II-g] in which $R^{18}$ is an alkyl group of 1 to 6 carbons substituted by a cyano group, and $R^{11}$, $R^{12}$, $R^{13}$, $R^{14}$, $Y^1$, and W are the same as above.

The reaction is conducted in a solvent in the presence of an acid or a base at 0 to 120° C., preferably 20 to 100° C., for several minutes to 12 hours, preferably 1 to 6 hours.

The acid or the base is used in an amount of 1 to 50 equivalents, preferably 1 to 20 equivalents, to one equivalent of the substrate substance.

The solvent includes ethers such as diethyl ether, tetrahydrofuran, dioxane, and dimethoxyethane; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, t-butanol; water, and the like.

The base includes inorganic bases such as lithium hydroxide, sodium hydroxide, potassium hydroxide, sodium carbonate, and potassium carbonate; and alkali metal alkoxides such as sodium methoxide, sodium ethoxide, potassium t-butoxide, and the like.

The acid includes formic acid, acetic acid, trifluoroacetic acid, hydrochloric acid, hydrobromic acid, sulfuric acid, and the like.

(Production Process 10-2)

The arylthiadiazole derivative of General Formula [II-g] in which $R^{18}$ is an alkyl group of 1 to 6 carbons which is substituted by a carbonyl group substituted by an alkoxyl group of 1 to 4 carbons, and $R^{11}$, $R^{12}$, $R^{13}$, $R^{14}$, $Y^1$, and W are the same as mentioned above can be produced by reaction, with an alcohol of 1 to 4 carbons, of the arylthiadiazole derivative represented by General Formula [II-g] in which $R^{18}$ is an alkyl group of 1 to 6 carbons substituted by a carboxyl group, and $R^{11}$, $R^{12}$, $R^{13}$, $R^{14}$, $Y^1$ and W are the same as above.

The reaction is conducted in a solvent in the presence of an acid at 0 to 120° C., preferably 20 to 100° C., for several minutes to 12 hours, preferably 1 to 6 hours.

The acid is used in an amount of 1 to 50 equivalents, preferably 1 to 20 equivalents to one equivalent of the substrate substance.

The solvent includes ethers such as diethyl ether, tetrahydrofuran, dioxane, and dimethoxyethane; polar solvents such as N,N-dimethylformamide, dimethylsulfoxide, 1,3-dimethyl-2-imidazolidinone, hexamethylphosphoric triamide, and acetonitrile; alcohols such as methanol, ethanol, isopropanol, t-butanol; water, and the like.

The acid includes formic acid, acetic acid, trifluoroacetic acid, hydrochloric acid, hydrobromic acid, sulfuric acid, and the like.

Specific examples of the arylthiadiazole derivatives represented by General Formula [I] or [II] are shown in Tables 1 to 26. However, the present invention is not limited thereto.

16

TABLE 1

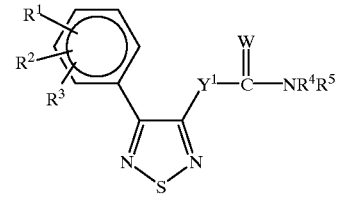

| Compound No. | $R^1$ | $R^2$ | $R^3$ | $Y^1$ | W | $NR^4R^5$ |
|---|---|---|---|---|---|---|
| 1 | H | H | 2-$NH_2$ | —O— | =O | —N(Me)(Me) |
| 2 | H | H | 2-$NH_2$ | —O— | =O | —N(Me)(Et) |
| 3 | H | H | 2-$NH_2$ | —O— | =O | —N(Me)(n-Pr) |
| 4 | H | H | 2-$NH_2$ | —O— | =O | —N(Me)(n-Bu) |
| 5 | H | H | 2-$NH_2$ | —O— | =O | —N(Me)(n-Hex) |
| 6 | H | H | 2-$NH_2$ | —O— | =O | —N(H)(n-Pr) |
| 7 | H | H | 2-$NH_2$ | —O— | =O | —N(Et)(Et) |
| 8 | H | H | 2-$NH_2$ | —O— | =O | —N(Me)($CH_2CH_2CN$) |
| 9 | H | H | 2-$NH_2$ | —O— | =O | pyrrolidinyl |
| 10 | H | H | 2-$NH_2$ | —O— | =O | —N(Me)(OMe) |

TABLE 2

| Compound No. | R¹ | R² | R³ | Y¹ | W | NR⁴R⁵ |
|---|---|---|---|---|---|---|
| 11 | H | H | 2-NH₂ | —O— | =O | 2-methylpiperidin-1-yl (N-methyl, 2-Me) |
| 12 | H | H | 2-NH₂ | —O— | =O | 2,6-dimethylpiperidin-1-yl |
| 13 | H | H | 2-NH₂ | —O— | =O | morpholin-4-yl |
| 14 | H | H | 2-NH₂ | —O— | =O | N(Me)(Ph) |
| 15 | H | H | 2-NH₂ | —O— | =O | N(Me)(4-MeO-C₆H₄) |
| 16 | H | H | 2-NH₂ | —O— | =O | N(Me)(4-Cl-C₆H₄) |
| 17 | H | H | 2-NH₂ | —O— | =O | N(Me)(CH₂Ph) |
| 18 | H | H | 2-NH₂ | —O— | =O | N(Me)(CH₂CH₂Ph) |
| 19 | H | H | 2-NH₂ | —O— | =O | N(Me)((CH₂)₃OMe) |

TABLE 2-continued
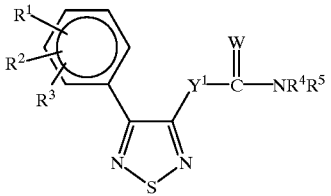
| Compound No. | R¹ | R² | R³ | Y¹ | W | NR⁴R⁵ |
|---|---|---|---|---|---|---|
| 20 | H | H | 2-NH$_2$ | —O— | =O | N(Me)(CH$_2$)$_3$OEt |
TABLE 3
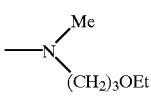
| Compound No. | R¹ | R² | R³ | Y¹ | W | NR⁴R⁵ |
|---|---|---|---|---|---|---|
| 21 | H | 2-Cl | 5-NH$_2$ | —O— | =O | N(Me)(Me) |
| 22 | H | 2-Cl | 5-NH$_2$ | —O— | =O | N(Me)(n-Pr) |
| 23 | H | 2-Cl | 5-NH$_2$ | —O— | =O | N(Me)(CH$_2$CH$_2$CN) |
| 24 | H | 2-Cl | 5-NHMe | —O— | =O | N(Me)(n-Pr) |
| 25 | H | 2-Cl | 5-NHMe | —O— | =O | N(Me)(CH$_2$CH$_2$CN) |
| 26 | H | 2-Cl | 5-NMe$_2$ | —O— | =O | N(Me)(n-Pr) |

TABLE 3-continued
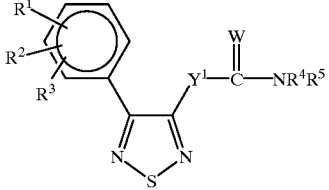
| Compound No. | R¹ | R² | R³ | Y¹ | W | NR⁴R⁵ |
|---|---|---|---|---|---|---|
| 27 | H | 2-Cl | 5-NMe₂ | —O— | =O | —N(Me)(CH₂CH₂CN) |
| 28 | H | 2-Cl | 5-CH₂OCH₂OMe | —O— | =O | —N(Me)(n-Pr) |
| 29 | H | 2-Cl | 5-CH₂OCH₂OMe | —O— | =O | —N(Me)(CH₂CH₂CN) |
| 30 | H | 2-Cl | 5-CH₂OSiMe₃ | —O— | =O | —N(Me)(n-Pr) |
TABLE 4
| Compound No. | R¹ | R² | R³ | Y¹ | W | NR⁴R⁵ |
|---|---|---|---|---|---|---|
| 31 | H | 2-Cl | 5-CH₂OSiMe₂ | —O— | =O | —N(Me)(CH₂CH₂CN) |
| 32 | H | 2-Cl | 5-CH₂OH | —O— | =O | —N(Me)(n-Pr) |
| 33 | H | 2-Cl | 5-CH₂OH | —O— | =O | —N(Me)(CH₂CH₂CN) |
| 34 | H | 2-Cl | 5-CN | —O— | =O | —N(Me)(n-Pr) |

TABLE 4-continued
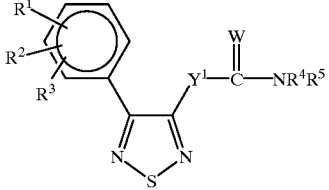
| Compound No. | R¹ | R² | R³ | Y¹ | W | NR⁴R⁵ |
|---|---|---|---|---|---|---|
| 35 | H | 2-Cl | 5-CN | —O— | =O | —N(Me)(CH₂CH₂CN) |
| 36 | H | 2-Cl | 5-CO₂H | —O— | =O | —N(Me)(n-Pr) |
| 37 | H | 2-Cl | 5-CO₂H | —O— | =O | —N(Me)(CH₂CH₂CN) |
| 38 | H | 2-Cl | 5-CO₂Me | —O— | =O | —N(Me)(n-Pr) |
| 39 | H | 2-Cl | 5-CO₂Me | —O— | =O | —N(Me)(CH₂CH₂CN) |
| 40 | H | 2-Cl | 5-CONH₂ | —O— | =O | —N(Me)(n-Pr) |
TABLE 5
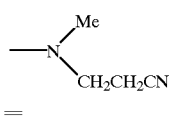
| Compound No. | R¹ | R² | R³ | Y¹ | W | NR⁴R⁵ |
|---|---|---|---|---|---|---|
| 41 | H | 2-Cl | 5-CONH₂ | —O— | =O | —N(Me)(CH₂CH₂CN) |

TABLE 5-continued
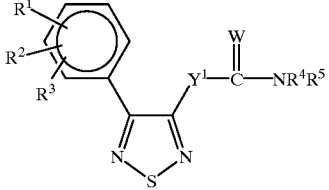
| Compound No. | R¹ | R² | R³ | Y¹ | W | NR⁴R⁵ |
|---|---|---|---|---|---|---|
| 42 | H | 2-Cl | 5-CONHMe | —O— | =O | —N(Me)(n-Pr) |
| 43 | H | 2-Cl | 5-CONHMe | —O— | =O | —N(Me)(CH₂CH₂CN) |
| 44 | H | 2-Cl | 5-CONMe₂ | —O— | =O | —N(Me)(n-Pr) |
| 45 | H | 2-Cl | 5-CONMe₂ | —O— | =O | —N(Me)(CH₂CH₂CN) |
TABLE 6
| Compound No. | R¹ | R² | R³ | Y¹ | W | NR⁴R⁵ |
|---|---|---|---|---|---|---|
| 46 | H | 2-Cl | 3-NH₂ | —O— | =O | —N(Me)(n-Pr) |
| 47 | H | 2-Cl | 3-NH₂ | —O— | =O | —N(Me)(CH₂CH₂CN) |
| 48 | H | 2-Cl | 3-NHMe | —O— | =O | —N(Me)(n-Pr) |

TABLE 6-continued

[Structure: phenyl ring with R¹, R², R³ substituents connected to a thiadiazole ring, connected via Y¹-C(=W)-NR⁴R⁵]

| Compound No. | R¹ | R² | R³ | Y¹ | W | NR⁴R⁵ |
|---|---|---|---|---|---|---|
| 49 | H | 2-Cl | 3-NHMe | —O— | =O | N(Me)(CH₂CH₂CN) |
| 50 | H | 2-Cl | 3-NMe₂ | —O— | =O | N(Me)(n-Pr) |
| 51 | H | 2-Cl | 3-NMe₂ | —O— | =O | N(Me)(CH₂CH₂CN) |
| 52 | H | 2-Cl | 3-CH₂OCH₂OMe | —O— | =O | N(Me)(n-Pr) |
| 53 | H | 2-Cl | 3-CH₂OCH₂OMe | —O— | =O | N(Me)(CH₂CH₂CN) |
| 54 | H | 2-Cl | 3-CH₂OSiMe₂ | —O— | =O | N(Me)(n-Pr) |

TABLE 7

[Structure: phenyl ring with R¹, R², R³ substituents connected to a thiadiazole ring, connected via Y¹-C(=W)-NR⁴R⁵]

| Compound No. | R¹ | R² | R³ | Y¹ | W | NR⁴R⁵ |
|---|---|---|---|---|---|---|
| 55 | H | 2-Cl | 3-CH₂OSiMe₃ | —O— | =O | N(Me)(CH₂CH₂CN) |

TABLE 7-continued

| Compound No. | R¹ | R² | R³ | Y¹ | W | NR⁴R⁵ |
|---|---|---|---|---|---|---|
| 56 | H | 2-Cl | 3-CH₂OH | —O— | =O | N(Me)(n-Pr) |
| 57 | H | 2-Cl | 3-CH₂OH | —O— | =O | N(Me)(CH₂CH₂CN) |
| 58 | H | 2-Cl | 3-CN | —O— | =O | N(Me)(n-Pr) |
| 59 | H | 2-Cl | 3-CN | —O— | =O | N(Me)(CH₂CH₂CN) |
| 60 | H | 2-Cl | 3-CO₂H | —O— | =O | N(Me)(n-Pr) |
| 61 | H | 2-Cl | 3-CO₂H | —O— | =O | N(Me)(CH₂CH₂CN) |
| 62 | H | 2-Cl | 3-CO₂Me | —O— | =O | N(Me)(n-Pr) |
| 63 | H | 2-Cl | 3-CO₂Me | —O— | =O | N(Me)(CH₂CH₂CN) |
| 64 | H | 2-Cl | 3-CONH₂ | —O— | =O | N(Me)(n-Pr) |

TABLE 8
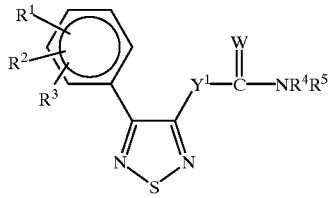
| Compound No. | R¹ | R² | R³ | Y¹ | W | NR⁴R⁵ |
|---|---|---|---|---|---|---|
| 65 | H | 2-Cl | 3-CONH₂ | —O— | =O | —N(Me)(CH₂CH₂CN) |
| 66 | H | 2-Cl | 3-CONHMe | —O— | =O | —N(Me)(n-Pr) |
| 67 | H | 2-Cl | 3-CONHMe | —O— | =O | —N(Me)(CH₂CH₂CN) |
| 68 | H | 2-Cl | 3-CONMe₂ | —O— | =O | —N(Me)(n-Pr) |
| 69 | H | 2-Cl | 3-CONMe₂ | —O— | =O | —N(Me)(CH₂CH₂CN) |
TABLE 9
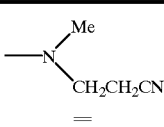
| Compound No. | R¹ | R² | R³ | Y¹ | W | NR⁴R⁵ |
|---|---|---|---|---|---|---|
| 70 | 2-Cl | 3-NH₂ | 6-Cl | —O— | =O | —N(Me)(Me) |
| 71 | 2-Cl | 3-NH₂ | 6-Cl | —O— | =O | —N(Me)(n-Pr) |

TABLE 9-continued

[Structure: phenyl ring with R¹, R², R³ substituents, connected to a 1,2,5-thiadiazole ring, with Y¹—C(=W)—NR⁴R⁵ group]

| Compound No. | R¹ R² | R³ | Y¹ | W | NR⁴R⁵ |
|---|---|---|---|---|---|
| 72 | 2-Cl 3-NH₂ | 6-Cl | —O— | =O | —N(Me)(CH₂CH₂CN) |
| 73 | 2-Cl 3-NH₂ | 6-Cl | —O— | =S | —N(Me)(n-Pr) |
| 74 | 2-Cl 3-NH₂ | 6-Cl | —O— | =S | —N(Me)(CH₂CH₂CN) |
| 75 | 2-Cl 3-NH₂ | 6-Cl | —S— | =O | —N(Me)(n-Pr) |
| 76 | 2-Cl 3-NH₂ | 6-Cl | —S— | =O | —N(Me)(CH₂CH₂CN) |
| 77 | 2-Cl 3-NHMe | 6-Cl | —O— | =O | —N(Me)(n-Pr) |
| 78 | 2-Cl 3-NHMe | 6-Cl | —O— | =O | —N(Me)(CH₂CH₂CN) |
| 79 | 2-Cl 3-NMe₂ | 6-Cl | —O— | =O | —N(Me)(n-Pr) |

TABLE 10
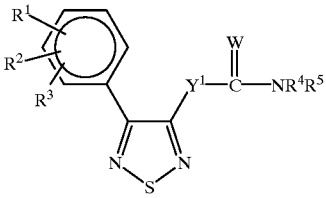
| Compound No. | R¹ | R² | R³ | Y¹ | W | NR⁴R⁵ |
|---|---|---|---|---|---|---|
| 80 | 2-Cl | 3-NMe₂ | 6-Cl | —O— | =O | —N(Me)(CH₂CH₂CN) |
| 81 | 2-Cl | 3-CH₂OCH₂OMe | 6-Cl | —O— | =O | —N(Me)(n-Pr) |
| 82 | 2-Cl | 3-CH₂OCH₂OMe | 6-Cl | —O— | =O | —N(Me)(CH₂CH₂CN) |
| 83 | 2-Cl | 3-CH₂OSiMe₃ | 6-Cl | —O— | =O | —N(Me)(n-Pr) |
| 84 | 2-Cl | 3-CH₂OSiMe₃ | 6-Cl | —O— | =O | —N(Me)(CH₂CH₂CN) |
| 85 | 2-Cl | 3-CH₂OH | 6-Cl | —O— | =O | —N(Me)(n-Pr) |
| 86 | 2-Cl | 3-CH₂OH | 6-Cl | —O— | =O | —N(Me)(CH₂CH₂CN) |
| 87 | 2-Cl | 3-CN | 6-Cl | —O— | =O | —N(Me)(n-Pr) |
| 88 | 2-Cl | 3-CN | 6-Cl | —O— | =O | —N(Me)(CH₂CH₂CN) |
| 89 | 2-Cl | 3-CO₂H | 6-Cl | —O— | =O | —N(Me)(n-Pr) |

TABLE 11

[Structure: phenyl ring with R¹, R², R³ substituents attached to a thiadiazole ring (N-S-N), with Y¹-C(=W)-NR⁴R⁵ group]

| Compound No. | R¹ | R² | R³ | Y¹ | W | NR⁴R⁵ |
|---|---|---|---|---|---|---|
| 90 | 2-Cl | 3-CO₂H | 6-Cl | —O— | =O | N(Me)(CH₂CH₂CN) |
| 91 | 2-Cl | 3-CO₂Me | 6-Cl | —O— | =O | N(Me)(n-Pr) |
| 92 | 2-Cl | 3-CO₂Me | 6-Cl | —O— | =O | N(Me)(CH₂CH₂CN) |
| 93 | 2-Cl | 3-CONH₂ | 6-Cl | —O— | =O | N(Me)(n-Pr) |
| 94 | 2-Cl | 3-CONH₂ | 6-Cl | —O— | =O | N(Me)(CH₂CH₂CN) |
| 95 | 2-Cl | 3-CONHMe | 6-Cl | —O— | =O | N(Me)(n-Pr) |
| 96 | 2-Cl | 3-CONHMe | 6-Cl | —O— | =O | N(Me)(CH₂CH₂CN) |
| 97 | 2-Cl | 3-CONMe₂ | 6-Cl | —O— | =O | N(Me)(n-Pr) |
| 98 | 2-Cl | 3-CONMe₂ | 6-Cl | —O— | =O | N(Me)(CH₂CH₂CN) |

TABLE 12

[Structure: phenyl ring with R¹, R², R³ substituents, attached to a 1,2,5-thiadiazole ring, with Y¹—C(=W)—NR⁴R⁵ group]

| Compound No. | R¹ | R² | R³ | Y¹ | W | NR⁴R⁵ |
|---|---|---|---|---|---|---|
| 99 | 2-Cl | 3-NH₂ | 6-F | —O— | =O | N(Me)(n-Pr) |
| 100 | 2-Cl | 3-NH₂ | 6-F | —O— | =O | N(Me)(CH₂CH₂CN) |
| 101 | 2-Cl | 3-NHMe | 6-F | —O— | =O | N(Me)(n-Pr) |
| 102 | 2-Cl | 3-NHMe | 6-F | —O— | =O | N(Me)(CH₂CH₂CN) |
| 103 | 2-Cl | 3-NMe₂ | 6-F | —O— | =O | N(Me)(n-Pr) |
| 104 | 2-Cl | 3-NMe₂ | 6-F | —O— | =O | N(Me)(CH₂CH₂CN) |
| 105 | 2-Cl | 3-CH₂OCH₂OMe | 6-F | —O— | =O | N(Me)(n-Pr) |
| 106 | 2-Cl | 3-CH₂OCH₂OMe | 6-F | —O— | =O | N(Me)(CH₂CH₂CN) |
| 107 | 2-Cl | 3-CH₂OSiMe₃ | 6-F | —O— | =O | N(Me)(n-Pr) |
| 108 | 2-Cl | 3-CH₂OSiMe₃ | 6-F | —O— | =O | N(Me)(CH₂CH₂CN) |

TABLE 13

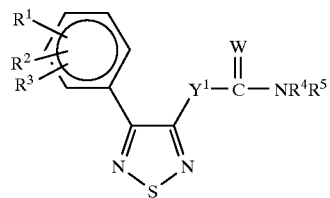

| Compound No. | R¹ | R² | R³ | Y¹ | W | NR⁴R⁵ |
|---|---|---|---|---|---|---|
| 109 | 2-Cl | 3-CH₂OH | 6-F | —O— | =O | —N(Me)(n-Pr) |
| 110 | 2-Cl | 3-CH₂OH | 6-F | —O— | =O | —N(Me)(CH₂CH₂CN) |
| 111 | 2-Cl | 3-CN | 6-F | —O— | =O | —N(Me)(n-Pr) |
| 112 | 2-Cl | 3-CN | 6-F | —O— | =O | —N(Me)(CH₂CH₂CN) |
| 113 | 2-Cl | 3-CO₂H | 6-F | —O— | =O | —N(Me)(n-Pr) |
| 114 | 2-Cl | 3-CO₂H | 6-F | —O— | =O | —N(Me)(CH₂CH₂CN) |
| 115 | 2-Cl | 3-CO₂Me | 6-F | —O— | =O | —N(Me)(n-Pr) |
| 116 | 2-Cl | 3-CO₂Me | 6-F | —O— | =O | —N(Me)(CH₂CH₂CN) |
| 117 | 2-Cl | 3-CONH₂ | 6-F | —O— | =O | —N(Me)(n-Pr) |

TABLE 13-continued

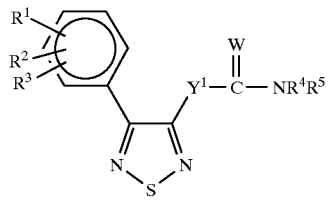

| Compound No. | R¹ | R² | R³ | Y¹ | W | NR⁴R⁵ |
|---|---|---|---|---|---|---|
| 118 | 2-Cl | 3-CONH₂ | 6-F | —O— | =O | —N(Me)(CH₂CH₂CN) |

TABLE 14

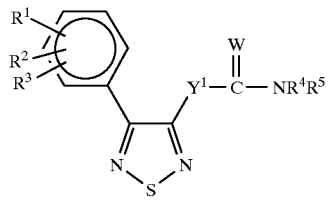

| Compound No. | R¹ | R² | R³ | Y¹ | W | NR⁴R⁵ |
|---|---|---|---|---|---|---|
| 119 | 2-Cl | 3-CONHMe | 6-F | —O— | =O | —N(Me)(n-Pr) |
| 120 | 2-Cl | 3-CONHMe | 6-F | —O— | =O | —N(Me)(CH₂CH₂CN) |
| 121 | 2-Cl | 3-CONMe₂ | 6-F | —O— | =O | —N(Me)(n-Pr) |
| 122 | 2-Cl | 3-CONMe₂ | 6-F | —O— | =O | —N(Me)(CH₂CH₂CN) |

TABLE 15

R11, R12, R13 on phenyl ring attached to 1,2,5-thiadiazole with N=C(R14)−NR9R10 substituent

| Compound No. | R11 | R12 | R13 | R14 | NR9R10 |
|---|---|---|---|---|---|
| 123 | H | H | H | H | N(Me)(Me) |
| 124 | H | H | 2-Cl | H | N(Me)(Me) |
| 125 | H | H | 2-Me | H | N(Me)(Me) |
| 126 | H | H | 2-MeO | H | N(Me)(Me) |
| 127 | H | 2-Cl | 6-Cl | H | N(Me)(Me) |
| 128 | H | 2-Cl | 6-Cl | H | N(Me)(n-Pr) |
| 129 | H | 2-Cl | 6-Cl | H | N(Me)(n-Hex) |
| 130 | H | 2-Cl | 6-Cl | H | N(Et)(Et) |
| 131 | H | 2-Cl | 6-Cl | Me | N(Et)(Et) |
| 132 | H | 2-Cl | 6-Cl | Ph | N(Et)(Et) |

TABLE 16

R11, R12, R13 on phenyl ring attached to 1,2,5-thiadiazole with Y1−SO2−NR9R10 substituent

| Compound No. | R11 | R12 | R13 | Y1 | NR9R10 |
|---|---|---|---|---|---|
| 133 | H | H | H | −O− | N(Me)(Me) |
| 134 | H | H | 2-Cl | −O− | N(Me)(Me) |
| 135 | H | H | 2-Me | −O− | N(Me)(Me) |
| 136 | H | H | 2-MeO | −O− | N(Me)(Me) |
| 137 | H | H | 2-NO2 | −O− | N(Me)(Me) |
| 138 | H | 2-Cl | 6-Cl | −O− | N(Me)(Me) |
| 139 | H | 2-Cl | 6-Cl | −O− | N(Me)(n-Pr) |
| 140 | H | 2-Cl | 6-Cl | −O− | N(Et)(Et) |
| 141 | H | 2-Cl | 6-Cl | −S− | N(Me)(Me) |

TABLE 16-continued

[Structure: phenyl(R11,R12,R13)-thiadiazole-Y1-SO2-NR9R10]

| Compound No. | R11 | R12 | R13 | Y1 | NR9R10 |
|---|---|---|---|---|---|
| 142 | H | 2-Cl | 6-Cl | —S— | N(Me)(n-Pr) |

TABLE 17

[Structure: phenyl(R11,R12,R13)-thiadiazole-Y1-CH2-aryl(J, R15, R16)]

| Compound No. | R11 | R12 | R13 | Y1 | aryl |
|---|---|---|---|---|---|
| 143 | H | H | H | —O— | 2-pyridyl |
| 144 | H | H | 2-Cl | —O— | 2-pyridyl |
| 145 | H | 2-Cl | 6-Cl | —O— | 2-pyridyl |
| 146 | H | 2-Cl | 6-Cl | —O— | 3-pyridyl |
| 147 | H | 2-Cl | 6-Cl | —O— | 2-Cl-phenyl |
| 148 | H | 2-Cl | 6-Cl | —O— | 2-OMe-phenyl |
| 149 | H | 2-Cl | 6-Cl | —O— | 2-NO2-phenyl |
| 150 | H | 2-Cl | 6-Cl | —O— | 4-Cl-2-NO2-phenyl |
| 151 | H | 2-Cl | 6-Cl | —S— | 2-pyridyl |
| 152 | H | 2-Cl | 6-Cl | —S— | 2-NO2-phenyl |

TABLE 18

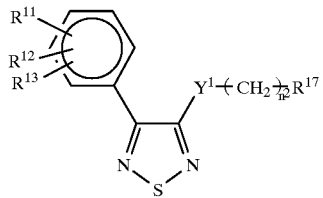

| Compound No. | R11 | R12 | R13 | Y1 | n2 | R17 |
|---|---|---|---|---|---|---|
| 153 | H | H | H | —O— | 1 | —SMe |
| 154 | H | H | 2-Cl | —O— | 1 | —SMe |
| 155 | H | 2-Cl | 6-Cl | —O— | 1 | —SMe |
| 156 | H | 2-Cl | 6-Cl | —O— | 1 | —OMe |
| 157 | H | 2-Cl | 6-Cl | —O— | 1 | —OCH₂CH₂OMe |
| 158 | H | 2-Cl | 6-Cl | —O— | 2 | —SMe |
| 159 | H | 2-Cl | 6-Cl | —O— | 2 | —OMe |
| 160 | H | 2-Cl | 6-Cl | —O— | 2 | —Br |
| 161 | H | 2-Cl | 6-Cl | —O— | 2 | —N(Me)(n-Pr) |
| 162 | H | 2-Cl | 6-Cl | —S— | 1 | —OCH₂CH₂OMe |

TABLE 19

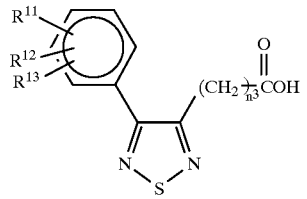

| Compound No. | R11 | R12 | R13 | n3 |
|---|---|---|---|---|
| 163 | H | H | 2-Cl | 0 |
| 164 | H | H | 3-Cl | 0 |
| 165 | H | H | 4-Cl | 0 |
| 166 | H | H | 2-Me | 0 |
| 167 | H | H | 3-Me | 0 |
| 168 | H | H | 4-Me | 0 |
| 169 | H | H | 2-F | 0 |
| 170 | H | H | 3-F | 0 |
| 171 | H | H | 4-F | 0 |
| 172 | H | H | 2-CF₃ | 0 |

TABLE 20

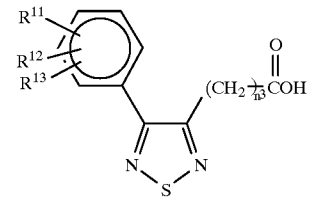

| Compound No. | R11 | R12 | R13 | n3 |
|---|---|---|---|---|
| 173 | H | H | 3-CF₃ | 0 |
| 174 | H | H | 4-CF₃ | 0 |
| 175 | H | H | 2-NO₂ | 0 |
| 176 | H | H | 3-NO₂ | 0 |
| 177 | H | H | 4-NO₂ | 0 |
| 178 | H | H | 2-MeO | 0 |
| 179 | H | H | 3-MeO | 0 |
| 180 | H | H | 4-MeO | 0 |
| 181 | H | H | 2-OH | 0 |
| 182 | H | H | 3-OH | 0 |

TABLE 21

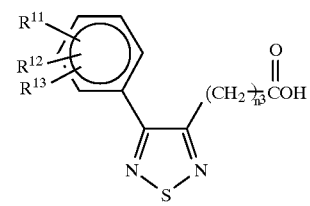

| Compound No. | R11 | R12 | R13 | n3 |
|---|---|---|---|---|
| 183 | H | H | 4-OH | 0 |
| 184 | H | 2-Cl | 6-Cl | 0 |
| 185 | H | H | 2-Cl | 1 |
| 186 | H | H | 2-Me | 1 |
| 187 | H | H | 2-F | 1 |
| 188 | H | H | 2-CF₃ | 1 |
| 189 | H | H | 2-NO₂ | 1 |
| 190 | H | H | 2-MeO | 1 |
| 191 | H | H | 2-OH | 1 |
| 192 | H | 2-Cl | 6-Cl | 1 |

TABLE 22

[Structure: phenyl ring with R¹¹, R¹², R¹³ substituents attached to a 1,2,5-thiadiazole ring, with -(CH₂)ₙ₃-C(=W)-NR⁴R⁵ side chain]

| Compound No. | $R^{11}$ | $R^{12}$ | $R^{13}$ | $n^3$ | W | $NR^4R^5$ |
|---|---|---|---|---|---|---|
| 193 | H | H | H | 0 | =O | —N(Me)(Me) |
| 194 | H | H | H | 0 | =O | —N(Me)(OMe) |
| 195 | H | H | 2-Cl | 0 | =O | —N(Me)(n-Pr) |
| 196 | H | H | 2-Cl | 0 | =S | —N(Me)(n-Pr) |
| 197 | H | H | 2-Cl | 0 | =O | —N(Me)(CH₂CH₂CN) |
| 198 | H | H | 2-Cl | 0 | =O | —NH—(2-F,4-Cl-phenyl) |
| 199 | H | 2-Cl | 6-Cl | 0 | =O | —N(Me)(n-Pr) |
| 200 | H | 2-Cl | 6-Cl | 0 | =O | —N(Me)(CH₂CH₂CN) |
| 201 | H | H | H | 1 | =O | —N(Me)(Me) |

TABLE 22-continued

[Structure: phenyl ring with R11, R12, R13 substituents attached to a 1,2,5-thiadiazole ring, with a (CH2)n3-C(=W)-NR4R5 group]

| Compound No. | R11 | R12 | R13 | n³ | W | NR⁴R⁵ |
|---|---|---|---|---|---|---|
| 202 | H | H | 2-Cl | 1 | =O | —N(Me)(n-Pr) |

TABLE 23

[Structure: phenyl ring with R11, R12, R13 substituents attached to a 1,2,5-thiadiazole ring, with a (CH2)n3-C(=W)-NR4R5 group]

| Compound No. | R11 | R12 | R13 | n³ | W | NR⁴R⁵ |
|---|---|---|---|---|---|---|
| 203 | H | H | 2-Cl | 1 | =S | —N(Me)(n-Pr) |
| 204 | H | H | 2-Cl | 1 | =O | —N(Me)(CH₂CH₂CN) |
| 205 | H | 2-Cl | 6-Cl | 1 | =O | —N(Me)(n-Pr) |
| 206 | H | 2-Cl | 6-Cl | 1 | =O | —N(Me)(CH₂CH₂CN) |

TABLE 24

[Structure: phenyl ring with R11, R12, R13 substituents attached to a 1,2,5-thiadiazole ring, with a Y¹-C(=W)-NR14R18 group]

| Compound No. | R11 | R12 | R13 | Y¹ | W | NR¹⁴R¹⁸ |
|---|---|---|---|---|---|---|
| 207 | H | H | H | —O— | =O | —N(Me)(CH₂CH₂CN) |
| 208 | H | H | 2-Cl | —O— | =O | —N(Me)(CH₂CH₂CN) |
| 209 | H | H | 3-Cl | —O— | =O | —N(Me)(CH₂CH₂CN) |
| 210 | H | H | 2-Me | —O— | =O | —N(Me)(CH₂CH₂CN) |
| 211 | H | H | 3-CF₃ | —O— | =O | —N(Me)(CH₂CH₂CN) |

TABLE 24-continued
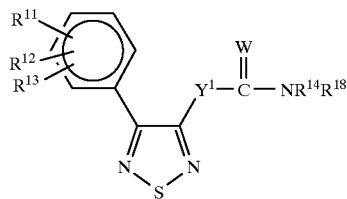
| Compound No. | $R^{11}$ | $R^{12}$ | $R^{13}$ | $Y^1$ | W | $NR^{14}R^{18}$ |
|---|---|---|---|---|---|---|
| 212 | H | H | 2-OMe | —O— | =O | —N(Me)CH₂CH₂CN |
| 213 | H | H | 2-OH | —O— | =O | —N(Me)CH₂CH₂CN |
| 214 | H | H | 2-NO₂ | —O— | =O | —N(Me)CH₂CH₂CN |
TABLE 24-continued
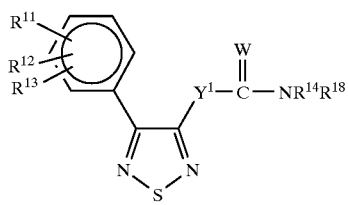
| Compound No. | $R^{11}$ | $R^{12}$ | $R^{13}$ | $Y^1$ | W | $NR^{14}R^{18}$ |
|---|---|---|---|---|---|---|
| 215 | H | 2-Cl | 6-F | —O— | =O | —N(Me)CH₂CH₂CN |
| 216 | H | 2-Cl | 5-NO₂ | —O— | =O | —N(Me)CH₂CH₂CN |
TABLE 25
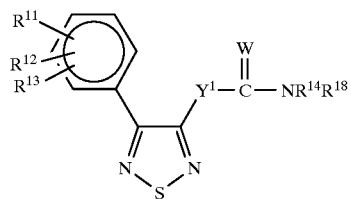
| Compound No. | $R^{11}$ | $R^{12}$ | $R^{13}$ | $Y^1$ | W | $NR^{14}R^{18}$ |
|---|---|---|---|---|---|---|
| 217 | H | 2-Cl | 5-OH | —O— | =O | —N(Me)CH₂CH₂CN |
| 218 | H | 2-Cl | 6-Cl | —O— | =O | —N(Me)CH₂CN |

TABLE 25-continued

[Structure: phenyl ring with R11, R12, R13 substituents connected to a 1,2,5-thiadiazole ring, which bears a Y1-C(=W)-NR14R18 group]

| Compound No. | R11 | R12 | R13 | Y1 | W | NR14R18 |
|---|---|---|---|---|---|---|
| 219 | H | 2-Cl | 6-Cl | —O— | =O | —N(Me)(CH₂CH₂CN) |
| 220 | H | 2-Cl | 6-Cl | —O— | =O | —N(Me)(CH₂CH₂OH) |
| 221 | H | 2-Cl | 6-Cl | —O— | =O | —N(Me)(CH₂CH₂COOH) |
| 222 | H | 2-Cl | 6-Cl | —O— | =O | —N(Me)(CH₂CH₂CH₂COOH) |
| 223 | H | 2-Cl | 6-Cl | —O— | =O | —N(Me)(CH₂CH₂CONH₂) |
| 224 | H | 2-Cl | 6-Cl | —O— | =O | —N(Me)(CH₂CH₂CO₂Et) |
| 225 | H | 2-Cl | 6-Cl | —O— | =S | —N(Me)(CH₂CH₂CN) |
| 226 | H | 2-Cl | 6-Cl | —S— | =O | —N(Me)(CH₂CH₂CN) |

TABLE 26

[Structure: phenyl ring with $R^{11}$, $R^{12}$, $R^{13}$ substituents attached to a 1,2,5-thiadiazole ring, with $Y^1-C(=W)-NR^{14}R^{18}$ group]

| Compound No. | $R^{11}$ | $R^{12}$ | $R^{13}$ | $Y^1$ | W | $NR^{14}R^{18}$ |
|---|---|---|---|---|---|---|
| 227 | H | 2-Cl | 6-Cl | —S— | =S | —N(Me)(CH$_2$CH$_2$CN) |
| 228 | 2-Cl | 3-Cl | 6-Cl | —O— | =O | —N(Me)(CH$_2$CH$_2$CN) |
| 229 | 2-Cl | 3-OH | 6-Cl | —O— | =O | —N(Me)(CH$_2$CH$_2$CN) |
| 230 | 2-Cl | 3-NO$_2$ | 6-Cl | —O— | =O | —N(Me)(CH$_2$CH$_2$CN) |
| 231 | 2-Cl | 3-NO$_2$ | 6-F | —O— | =O | —N(Me)(CH$_2$CH$_2$CN) |

The arylthiadiazole derivatives represented by. General Formulas [I] and [II], and salts thereof have useful pharmaceutical properties, in particular, antiviral effects. The medical composition containing the above compound is useful for curative treatment of virus-infected patients, or preliminary treatment of persons who may possibly be infected with a virus.

The DNA type viruses which will be killed by the virucide of the present invention include Herpes simplex virus type 1, Herpes simplex virus type 2, Human cytomegalovirus, Epstein-Barr virus, Varicella zoster virus, and Human herpes virus 6 of Herpesviridae family; Human adenovirus of Adenoviridae family; Hepatitis B virus of Hepadnaviridae family; Human papilloma virus of Papovaviridae family, and the like.

The RNA type viruses which will be killed by the virucide of the present invention include Rubella virus, Japanese encephalitis virus, and Hepatitis C virus of Togaviridae family; Measles virus, Respiratory syncytial virus, and Humps virus of Paramyxoviridae family; Influenza virus of Orthomyxoviridae family; Rabies virus of Rhabdoviridae family; Human T-lymphotropic virus, and Human immunodeficiency virus of Retroviridae family; Human polio virus, and Hepatitis A virus of Picornaviridae family; and the like. In particular, the virucide of the present invention is effective against Human immunodeficiency virus (HIV).

The arylthiadiazole derivative represented by General Formula [I] or [II], or the salt thereof as the virucide can be dosed by oral administration, parenteral administration (hypodermic, intravenous, intramuscular, and sternum injection), or intrarectal administration. For the administration, the arylthiadiazole derivative represented by General Formula [I] or [II], or the salt thereof is dosed in a state of a formulation prepared by mixing with a suitable carrier. The formulation includes tablets, granules, fine grains, powders, capsules, injection, ophthalmic solutions, ophthalmic ointments, and suppositories. The active ingredient is contained in the formulation at a content of from about 0.01 to 99.99%. The dosage depends on the kind of the objective virus, the symptom, the patient's age, and the dosing method, and is usually in the range of from about 0.01 to 500 mg/kg/day in terms of the active ingredient.

The present invention is described specifically by reference to examples without limiting the invention thereto.

EXAMPLE 1

Production of N,N-dimethyl [3-(3-amino-2,6-dichlorophenyl)-1,2,5-thiadiazol-4-yl] carbamate (Compound 70)

In 10 mL of ethanol, was dissolved 100 mg of N,N-dimethyl [3-(2,6-dichloro-3-nitrophenyl)-1,2,5-thiadiazol- 4-yl] carbamate. To this solution, 10 mg of platinum oxide, and 0.1 mL of acetic acid were added, and the mixture was stirred in a hydrogen atmosphere at room temperature. After stirring for 2 hours, the liquid reaction mixture was filtered through Celite. The filtrate is concentrated, and purified by preparative silica gel thin layer chromatography to obtain 80 mg of N,N-dimethyl [3-(3-amino-2,6-dichlorophenyl)-1,2,5-thiadiazol-4-yl] carbamate.

Melting Point: 120–123° C.

$^1$H-NMR (Solvent: CDCl$_3$, Unit: δ ppm): 2.90 (s, 3H), 2.95 (s, 3H), 4.3 (br s, 2H), 6.80 (d, J=9 Hz, 1H), 7.16 (d, J=9 Hz, 1H) IR (KBr, cm$^{-1}$): 3480, 3460, 3390, 3350, 1740, 1620, 1460, 1370, 1325, 1220, 1150, 815

Typical compounds were prepared in the same manner as in Example 1. The properties are shown in Examples 2–5.

EXAMPLE 2

N,N-Dimethyl [3-(5-amino-2-chlorophenyl)-1,2,5-thiadiazol-4-yl] carbamate (Compound 21)

Melting Point: 121–124° C.

$^1$H-NMR (Solvent: CDCl$_3$, Unit: δ ppm) 2.93 (s, 3H), 3.03 (s, 3H), 3.4 (br s, 2H), 6.70 (dd, J=3, 8.5 Hz, 1H), 6.76 (d, J=3 Hz, 1H), 7.22 (d, J=8.5 Hz, 1H) IR (KBr, cm$^{-1}$) 3440, 3340, 1730, 1595, 1455, 1375, 1160, 810

EXAMPLE 3

N-Methyl-N-propyl [3-(3-amino-2-chloro-6-fluorophenyl)-1,2,5-thiadiazole-4-yl] carbamate (Compound 99)

Oily matter $^1$H-NMR (Solvent: CDCl$_3$, Unit: δ ppm): [0.80 (t, J=7.5 Hz), 0.81 (t, J=7.5 Hz), 3H], [1.48 (sextet, J=7.5 Hz), 1.50 (sextet, J=7.5 Hz), 2H], [2.91 (s), 2.95 (s), 3H], [3.20 (t, J=7.5 Hz), 3.25 (t, J=7.5 Hz), 2H], 3.9 (br s, 2H), 6.7–7.1 (m, 2H) IR (neat, cm$^{-1}$): 3470, 3360, 1735, 1475, 1385, 1210, 1150

EXAMPLE 4

N-Methyl-N-propyl [3-(3-amino-2,6-dichlorophenyl)-1,2,5-thiadiazol-4-yl] carbamate (Compound 71)

Oily matter $^1$H-NMR (Solvent: CDCl$_3$, Unit: δ ppm): [0.75 (t, J=7.5 Hz), 0.76 (t, J=7.5 Hz), 3H], [1.44 (sextet, J=7.5 Hz), 1.45 (sextet, J=7.5 Hz), 2H], [2.89 (s), 2.90 (s), 3H], [3.16 (t, J=7.5 Hz), 3.21 (t, J=7.5 Hz), 2H], 4.26 (br s, 2H), [6.78 (d, J=9 Hz), 6.79 (d, J=9 Hz), 1H], 7.14 (d, J=9 Hz, 1H) IR (neat, cm$^{-1}$): 3480, 3360, 1740, 1620, 1460, 1380, 1220, 1150

EXAMPLE 5

N-Methyl-N-propyl [3-(5-amino-2-chlorophenyl)-1,2,5-thiadiazol-4-yl] carbamate (Compound 22)

Oily matter $^1$H-NMR (Solvent: CDCl$_3$, Unit: δ ppm): [0.81 (t, J=7.5 Hz), 0.83 (t, J=7.5 Hz), 3H], [1.50 (sextet, J=7.5 Hz), 1.53 (sextet, J=7.5 Hz), 2H], [2.91 (s), 2.99 (s), 3H], [3.20 (t, J=7.5 Hz), 3.29 (t, J=7.5 Hz), 2H], 3.70 (br s, 2H), [6.68 (dd, J=3, 8.5 Hz), 6.74 (d, J=3 Hz), 6.75 (d, J=3 Hz), 1H], 7.20(d, J=8.5 Hz, 1H) IR (neat, cm$^{-1}$): 3460, 3360, 1735, 1460, 1390, 1305, 1210, 1150

EXAMPLE 6

Production of N$^1$-diethyl-N$^2$-[3-(2,6-dichlorophenyl)-1,2,5-thiadiazol-4-yl]formamidine (Compound 130)

0.2 Gram of N,N-diethylformamide was dissolved in 1 mL of benzene. Thereto 0.15 g of phosphorus oxychloride was added. The mixture was stirred at room temperature for 12 hours. To this reaction mixture, 0.12 g of 3-(2,6-dichlorophenyl)-4-amino-1,2,5-thiadiazole was added, and the mixture was refluxed by heating for one hour. Then the mixture was left standing to allow it to cool to room temperature. The reaction mixture was poured into water, and was extracted with ether. The ether layer was washed by 10% sodium hydrodgencarbonate twice, and by water twice, dried over anhydrous magnesium sulfate, and was concentrated. The concentrate was purified by silica gel column chromatography to obtain 0.15 g of N$^1$-diethyl-N$^2$-[3-(2,6-dichlorophenyl)-1,2,5-thiadiazol-4-yl]formamidine.

Oily matter $^1$H-NMR (Solvent: CDCl$_3$, Unit: δ ppm): 1.00 (t, J=7 Hz, 3H,), 1.17 (t, J=7 Hz, 3H), [3.28 (q, J=7 Hz), 3.30 (q, J=7 Hz), 4H], 7.2–7.4 (m, 3H), 8.32 (s, 1H) IR (neat, cm$^{-1}$): 1610, 1485, 1460, 1425, 1395, 1360, 1125, 795

Typical compounds were prepared in the same manner as in Example 6. The properties are shown in Examples 7–10.

EXAMPLE 7

N$^1$-Dimethyl-N$^2$-[3-(2,6-dichlorophenyl)-1,2,5-thiadiazol-4-yl] formamidine (Compound 127)

Melting Point: 100–103° C.

$^{-1}$H-NMR (Solvent: CDCl$_3$, Unit: δ ppm): 2.88 (s, 3H), 3.04 (s, 3H), 7.2–7.4 (m, 3H), 8,35 (s, 1H) IR (KBr, cm$^{-1}$): 1630, 1505, 1470, 1430, 1390, 1120, 1105, 795

EXAMPLE 8

N$^1$-methyl-N$^1$-propyl-N$^2$-[3-(2,6-dichlorophenyl)-1,2,5-thiadiazol-4-yl]formamidine (Compound 128)

Oily matter $^1$H-NMR (Solvent: CDCl$_3$, Unit: δ ppm): 0.73 (t, J=7 Hz, 1H,), 0.88 (t, J=7 Hz, 2H), 1.4–1.7 (m, 2H), 2.86 (s, 2H), 3.02 (s, 1H), 3.25 (q, J=7 Hz, 2H), 7.2–7.4 (m, 3H), 8.35 (s, 1H) IR (neat, cm$^{-1}$): 1615, 1490, 1465, 1430, 1390, 1125, 795

EXAMPLE 9

N$^1$-diethyl-N$^2$-[3-(2,6-dichlorophenyl)-1,2,5-thiadiazol-4-yl]acetamidine (Compound 131)

Melting point: 39–40° C.

$^1$H-NMR (Solvent: CDCl$_3$, Unit: δ ppm) 0.85 (br s, 3H), 1.11 (br s, 3H), 2.20 (s, 3H), 3.29 (q, J=7 Hz, 4H), 7.2–7.4 (m, 3H) IR (KBr, cm$^{-1}$): 1560, 1550, 1425, 1390, 1355, 790

EXAMPLE 10

N$^1$-diethyl-N$^2$-[3-(2,6-dichlorophenyl)-1,2,5-thiadiazol-4-yl]benzamidine (Compound 132)

Melting point: 54–55° C.

$^1$H-NMR (Solvent: CDCl$_3$, Unit: δ ppm): 0.99 (t, J=7 Hz, 6H), 3.03 (br, q, J=7 Hz, 2H), 3.49 (br q, J=7 Hz, 2H), 7.1–7.5 (m, 8H) IR (KBr, cm$^{-1}$): 1565, 1555, 1425, 1390, 1360, 790, 780

EXAMPLE 11

Production of 4-(2-chlorophenyl)-1,2,5-thiadiazole-3-carboxylic acid (Compound 163)

In 1,3-dimethyl-2-imidazolidinone, were stirred 280 mg of 3-bromo-4-(2-chlorophenyl)-1,2,5-thiadiazole, and 180 mg of copper cyanide at 150° C. for 12 hours. After spontaneous cooling, the reaction mixture was poured into water, and the mixture was extracted with diethyl ether. The diethyl layer was washed with dilute sodium hydroxide solution and water, dried over anhydrous magnesium sulfate, and concentrated. The concentrate was purified by silica gel column chromatography to obtain 120 mg of 3-(2-chlorophenyl)-4-cyano-1,2,5-thiadiazole. The obtained 3-(2-chlorophenyl)-4-cyano-1,2,5-thiadiazole (120 mg) was heated with 6 mL of 5% sodium hydroxide solution and 2 mL of ethanol, and refluxed for one hour. After spontaneous cooling, the reaction mixture was poured into a dilute hydrochloric acid solution, and the mixture was extracted with diethyl ether. The diethyl ether layer was washed with water, dried over anhydrous magnesium sulfate, and concentrated. The concentrate was purified by silica gel column chromatography to obtain 100 mg of 4-(2-chlorophenyl)-1,2,5-thiadiazole-3-carboxylic acid.
Melting point: 112–114° C.
IR (KBr, cm$^{-1}$): 3600–2400, 1705, 1270, 1240, 1165, 750 Elemental analysis (%) as $C_9H_5ClN_2O_2S$ Calculated: C: 44.92, H: 2.09, N: 11.64 Found: C: 44.64, H: 2.19, N: 11.52

Typical compounds were prepared in the same manner as in Example 11. The properties are shown in Examples 12–22.

EXAMPLE 12

4-(3-Chlorophenyl)-1,2,5-thiadiazole-3-carboxylic acid (Compound 164)
Melting point: 163–165° C.
IR (KBr, cm$^{-1}$): 3200–2400, 1700, 1460, 1270, 1160, 770 Elemental analysis (%) as $C_9H_5ClN_2O_2S$ Calculated: C: 44.92, H: 2.09, N: 11.64 Found: C: 44.94, H: 2.38, N: 11.84

EXAMPLE 13

4-(4-Chlororhenyl)-1,2,5-thiadiazole-3-carboxylic acid (Comound 165)
Melting point: 157–158° C.
IR (KBr, cm$^{-1}$): 3300–2400, 1700, 1465, 1440, 1295, 1160, 1090, 820 Elemental analysis (%) as $C_9H_5ClN_2O_2S$ Calculated: C: 44.92, H: 2.09, N: 11.64 Found: C: 44.68, H: 2.32, N: 11.51

EXAMPLE 14

4-(2-Tolyl)-1,2,5-thiadiazole-3-carboxylic acid (Compound 166)
Melting point: 119–121° C.
IR (KBr, cm$^{-1}$) 3300–2400, 1700, 1460, 1450, 1260, 1155, 850, 765, 745 Elemental analysis (%) as $C_{10}H_8N_2O_2S$ Calculated: C: 54.53, H: 3.66, N: 12.72 Found: C: 54.29, H: 3.89, N: 12.71

EXAMPLE 15

4-(3-Tolyl)-1,2,5-thiadiazole-3-carboxylic acid (Compound 167)
Melting point: 118–120° C.
IR (KBr, cm$^{-1}$): 3200–2400, 1700, 1460, 1450, 1280, 1140, 770 Elemental analysis (%) as $C_{10}H_8N_2O_2S$ Calculated: C: 54.53, H: 3.66, N: 12.72 Found: C: 54.42, H: 3.56, N: 12.71

EXAMPLE 16

4-(4-Tolyl)-1,2,5-thiadiazole-3-carboxylic acid (Compound 168)
Melting point: 128–130° C.
IR (KBr, cm$^{-1}$): 3300–2400, 1700, 1455, 1435, 1295, 1150 Elemental analysis (%) as $C_{10}H_8N_2O_2S$ Calculated: C: 54.53, H: 3.66, N: 12.72 Found: C: 54.33, H: 3.62, N: 12.59

EXAMPLE 17

4-(3-Fluorophenyl)-1,2,5-thiadiazole-3-carboxylic acid (Compound 170)
Melting point: 153–156° C.
IR (KBr, cm$^{-1}$): 3200–2400, 1700, 1460, 1210, 870, 855, 770 Elemental analysis (%) as $C_9H_5FN_2O_2S$ Calculated: C: 48.21, H: 2.25, N: 12.49 Found: C: 48.04, H: 2.54, N: 12.69

EXAMPLE 18

4-(4-Fluorophenyl)-1,2,5-thiadiazole-3-carboxylic acid (Compound 171)
Melting point: 165–166° C.
IR (KBr, cm$^{-1}$): 3300–2400, 1700, 1460, 1440, 1220, 1160, 830 Elemental analysis (%) as $C_9H_5FN_2O_2S$ Calculated: C: 48.21, H: 2.25, N: 12.49 Found: C: 47.97, H: 2.47, N: 12.48

EXAMPLE 19

4-(3-Trifluoromethylphenyl)-1,2,5-thiadiazole-3-carboxylic acid (Compound 173)
Melting point: 122–124° C.
IR (KBr, cm$^{-1}$) 3200–2400, 1700, 1325, 1295, 1155, 1110 Elemental analysis (%) as $C_{10}H_5F_3N_2O_2S$ Calculated: C: 43.80, H: 1.84, N: 10.22 Found: C: 43.63, H: 2.13, N: 10.41

EXAMPLE 20

4-(4-Trifluoromethylphenyl)-1,2,5-thiadiazole-3-carboxylic acid (Compound 174)
Melting point: 135–137° C.
IR (KBr, cm$^{-1}$): 3200–2400, 1700, 1460, 1320, 1160, 1110 Elemental analysis (%) as $C_{10}H_5F_3N_2O_2S$ Calculated: C: 43.80, H: 1.84, N: 10.22 Found: C: 43.56, H: 2.06, N: 10.20

EXAMPLE 21

4-(3-Nitrophenyl)-1,2,5-thiadiazole-3-carboxylic acid (Compound 176)
Melting point: 193–194° C.
IR (KBr, cm$^{-1}$): 3400–2400, 1705, 1525, 1465, 1340 Elemental analysis (%) as $C_9H_5N_3O_4S$ Calculated: C: 43.03, H: 2.01, N: 16.73 Found: C: 42.86, H: 2.29, N: 16.92

EXAMPLE 22

4-(4-Methoxyphenyl)-1,2,5-thiadiazole-3-carboxylic acid (Compound 180)
Melting point: 118–120° C.
IR (KBr, cm$^{-1}$): 3200–2400, 1700, 1605, 1460, 1440, 1250, 1155 Elemental analysis (%) as $C_{10}H_8N_2O_3S$ Calculated: C: 50.84, H: 3.41, N: 11.86 Found: C: 50.60, H: 3.64, N: 11.85

EXAMPLE 23

Production of N-methyl-N-propyl 4-(2-chlorophenyl)-1,2,5-thiadiazole-3-carboxamide (Compound 195)

In 1 mL of dichloromethane, was dissolved 50 mg of 4-(2-chlorophenyl)-1,2,5-thiadiazole-3-carboxylic acid. To this solution, 70 mg of thionyl chloride was added. The solution was stirred for one hour. After spontaneous cooling to room temperature, unreacted thionyl chloride was distilled off under a reduced pressure. To the distillation residue, 1 mL of dichloromethane, 73 mg of methylpropylamine were added, and the mixture was stirred at room temperature for 6 hours. Then the reaction mixture was poured into water, and the mixture was extracted with dichloromethane. The dichloromethane layer was washed with two portions respectively of dilute hydrochloric acid, 10% sodium hydrogencarbonate, and water, dried over anhydrous magnesium sulfate, and concentrated. The concentrate was purified by preparative silica gel thin layer chromatography to obtain 50 mg of N-methyl-N-propyl 4-(2-chlorophenyl)-1,2,5-thiadiazole-3-carboxamide.
Oily matter
$^1$H-NMR (Solvent: CDCl$_3$, Unit: δ ppm) [0.85 (t, J=7.5 Hz), 0.88 (t, J=7.5 Hz), 3H], 1.5–1.8 (m, 2H), [3.02 (s), 3.03 (s), 3H], [3.21 (t, J=7.5 Hz), 3.21 (dd, J=6, 9 Hz), 1H], [3.43 (t, J=7.5 Hz), 3.43 (dd, J=6.9 Hz), 1H], 7.3–7.6 (m, 4H)

Typical compounds were produced in the same manner as in Example 23. The properties are shown in Examples 24–25.

EXAMPLE 24

N-Methoxy-N-methyl 4-phenyl-1,2,5-thiadiazole-3-carboxamide (Compound 194)
$^1$H-NMR (Solvent: CDCl$_3$, Unit: δ ppm):
3.3(s, 3H), 3.5 (s, 3H), 7.2–7.9 (m, 5H) IR (KBr, cm$^1$): 1655, 1480, 1430, 1360, 970, 750

EXAMPLE 25

N-(4-Chloro-2-fluorophenyl) 4-(4-chlorophenyl)-1,2,5-thiadiazole-3-carboxamide (Compound 198)

$^1$H-NMR (Solvent: CDCl$_3$, Unit: δ ppm): 7.0–7.8 (m, 6H), 8.3 (t, J=8 Hz, 1H), 9.1 (br s, 1H) IR (KBr, cm$^{-1}$): 1690, 1590, 1520, 1480, 1410, 820

EXAMPLE 26

Production of [3-(2-chlorophenyl)-1,2,5-thiadiazole-4-yl] acetic acid (Compound 185)

In N,N-dimethylformamide, 290 mg of 3-bromomethyl-4-(2-chlorophenyl)-1,2,5-thiadiazole, and 49 mg of sodium cyanide were stirred at 90° C. for 3 hours. After spontaneous cooling, the reaction mixture was poured into water, and was extracted with diethyl ether. The diethyl ether layer was washed with dilute sodium hydroxide solution and water, dried over anhydrous magnesium sulfate, and concentrated. The concentrate was purified by silica gel column chromatography to obtain 150 mg of 3-(2-chlorophenyl)-4-cyanomethyl- 1,2,5-thiadiazole. The obtained 150 mg of 3-(2-chlorophenyl)-4-cyanomethyl-1,2,5-thiadiazole, 6 mL of 5% sodium hydroxide solution, and 2 mL of ethanol were mixed and refluxed by heating for one hour. After spontaneous cooling, the reaction mixture was poured into dilute hydrochloric acid, and was extracted with diethyl ether. The diethyl ether layer was washed with water, dried over anhydrous magnesium sulfate, and concentrated. The concentrate was purified by silica gel column chromatography to obtain 120 mg of [3-(2-chlorophenyl)-1,2,5-thiadiazole-4-yl]acetic acid.

$^1$H-NMR (Solvent: CDCl$_3$, Unit: δ ppm) 3.95 (s, 2H), 7.3–7.6 (m, 3H), 8.4 (br s, 1H)

EXAMPLE 27

Production of N-methyl-N-propyl [3-(2-chlorophenyl)-1,2,5-thiadiazol-4-yl]acetamide (Compound 202)

In 1 mL of dichloromethane, was dissolved 30 mg of [3-(2-chlorophenyl)-1,2,5-thiadiazol-4-yl]acetic acid. To this solution, 60 mg of thionyl chloride was added. The mixture was stirred for one hour. After spontaneous cooling to room temperature, unreacted thionyl chloride was distilled off under a reduced pressure. To the distillation residue, 1 mL of dichloromethane, 73 mg of methylpropylamine were added, and the mixture was stirred at room temperature for 6 hours. Then the reaction mixture was poured into water, and was extracted with dichloromethane. The dichloromethane layer was washed with two portions respectively of dilute hydrochloric acid, 10% sodium hydrogencarbonate solution, and water, dried over anhydrous magnesium sulfate, and concentrated. The concentrate was purified by preparative silica gel thin layer chromatography to obtain 20 mg of N-methyl-N-propyl [3-(2-chlorophenyl)-1,2,5-thiadiazol-4-yl]acetamide.

Oily matter, $^1$H-NMR (Solvent: CDCl$_3$, Unit: δ ppm): [0.82 (t, J=7.5 Hz), 0.83 (t, J=7.5 Hz), 3H], 1.3–1.6 (m, 2H), [2.86 (s), 2.97 (s), 3H], [3.21 (t, J=7.5 Hz), 3.28 (t, J=7.5 Hz), 2H], 3.92 (s, 2H), 7.3–7.6 (m, 4H)

EXAMPLE 28

Producition of N-(3-carboxypropyl)-N-methyl [3-(2,6-dichlorophenyl)-1,2,5-thiadiazol-4-yl] carbamate (Compound 222)

In 10 mL of dichloromethane, were dissolved 490 mg of 3-(2,6-dichlorophenyl)-4-hydroxy-1,2,5-thiadiazole, and 210 mg of bis(trichloromethyl) carbonate. Thereto, 170 mg of pyridine was added. The mixture was stirred at room temperature for 12 hours. Thereto, 340 mg of 4-(methylamino)butyric acid hydrochloride, and 570 mg of N,N-diisopropylethylamine were added. The mixture was stirred at room temperature for 12 hours. The reaction mixture was poured into water, and was extracted with dichloromethane. The dichloromethane layer was washed with dilute hydrochloric acid, and water successively, dried over anhydrous magnesium sulfate, and concentrated. The concentrate was purified by silica gel column chromatography to obtain 510 mg of N-(3-carboxypropyl)-N-methyl [3-(2,6-dichlorophenyl)-1,2,5-thiadiazol-4-yl] carbamate.

Melting point: 125–126° C.

$^1$H-NMR (Solvent: CDCl$_3$, Unit: δ ppm) 1.6–1.9 (m, 2H), 2.1–2.3 (m, 2H), [2.90 (s), 2.95 (s), 3H], [3.26 (t, J=7.0 Hz), 3.32 (t, J=7.0 Hz), 2H], 7.2–7.5 (m, 3H), 8.5 (br 5, 1H) IR (KBr, cm$^{-1}$) 3400–2400, 1740, 1700, 1430, 1380, 1295, 1230, 1180, 790

A typical compound was produced in the same manner as in Example 28. The properties of the compound are shown in Example 29.

EXAMPLE 29

N-(cyanomethyl)-N-methyl [3-(2,6-dichlorophenvl)-1,2,5-thiadiazol-4-yl] carbamate (Compound 218)

Melting point: 106–107° C.

$^1$H-NMR (Solvent: CDCl$_3$, Unit: δ ppm): [3.02 (s), 3.09 (s), 3H], [4.20 (s), 4.25 (s), 2H], 7.3–7.5 (m, 3H) IR (KBr, cm$^{-1}$): 2250, 1745, 1430, 1380, 1280, 1230, 1205, 1135, 790, 770

EXAMPLE 30

Production of N-(2-cyanoethyl)-N-methyl [3-(2,6-dichlorophenyli-1,2,5-thiadiazol-4-yl] carbamate (Compound 219)

In 50 mL of dichloromethane, were dissolved 1.98 g of 3-(2,6-dichlorophenyl)-4-hydroxy-1,2,5-thiadiazole, and 0.8 g of bis(trichloromethyl) carbonate. Thereto, 0.7 g of pyridine was added. The mixture was stirred at room temperature for 12 hours. Thereto, 1.51 g of N-(2-cyanoethyl)-N-methylamine was added. The mixture was stirred at room temperature for 12 hours. The reaction mixture was poured into water, and was extracted with dichloromethane. The dichloromethane layer was washed with dilute hydrochloric acid, 10% sodium hydrogencarbonate, and water successively, dried over anhydrous magnesium sulfate, and concentrated. The concentrate was purified by silica gel column chromatography to obtain 2.8 g of N-(2-cyanoethyl)-N-methyl [3-(2,6-dichlorophenyl)-1,2,5-thiadiazo1–4-yl] carbamate.

Oily matter $^1$H-NMR (Solvent: CDCl$_3$, Unit: δ ppm): [2.46 (t, J=6.5 Hz), 2.51 (t, J=6.5 Hz), 2H], [3.04 (s), 3.12 (s), 3H], [3.49 (t, J=6.5 Hz), 3.59 (t, J=6.5 Hz), 2H], 7.3–7.55 (m, 3H) IR (neat, cm$^{-1}$): 2250, 1740, 1430, 1380, 1230, 1195, 1125, 790

A typical compound was produced in the same manner as in Example 30. The properties of the compound are shown in Example 31.

EXAMPLE 31

N-(2-Hydroxyethyl)-N-methyl [3-(2,6-dichlorophenyl)-1,2, 5-thiadiazol-4-yl] carbamate (Compound 220)

Melting point: 105–106° C.

$^1$H-NMR (Solvent: CDCl$_3$, Unit: δ ppm): 2.1 (br s, 1H), [2.97 (s), 3.02 (s), 3H], [3.36 (t, J=5.5 Hz), 3.41 (t, J=5.5 Hz), 2H], 3.64 (t, J=5.5 Hz, 2H), 7.3–7.5 (m, 3H) IR (KBr, cm$^{-1}$): 3550, 1725, 1430, 1380, 1220, 1130, 790

The properties of compounds produced in the same manner as in Example 30 are shown in Examples 32, and 33.

EXAMPLE 32
N-Methyl-N-propyl [3-(2,6-dichloro-3-cyanophenyl)-1,2,5-thiadiazol-4-yl] carbamate (Compound 87)

Oily matter $^1$H-NMR (Solvent: CDCl$_3$, Unit: δ ppm): [0.76 (t, J=7.4 Hz), 0.80 (t, J=7.4 Hz), 3H], [1.46 (sextet, J=7.4 Hz), 1.50 (sextet, J=7.4 Hz), 2H], [2.89 (s), 2.96 (s), 3H], [3.18 (t, J=7.4 Hz), 3.25 (t, J=7.4 Hz), 2H], 7.55 (d, J=8.5 Hz, 1H), [7.71 (d, J=8.5 Hz), 7.73 (d, J=8.5Hz), 1H] IR (neat, cm$^{-1}$): 2230, 1740, 1395, 1365, 1145

EXAMPLE 33
N-Methyl-N-propyl [3-(2,6-dichloro-3-methoxycarbonylphenyl)-1,2,5-thiadiazol-4-yl] carbamate (Compound 91)

Oily matter $^1$H-NMR (Solvent: CDCl$_3$, Unit: δ ppm): [0.75 (t, J=7.4 Hz), 0.77 (t, J=7.4 Hz), 3H], [1.40 (t, J=7.4 Hz, 3H), 1.45 (sextet, J=7.4 Hz, 2H), [2.90 (s), 2.93 (s), 3H], [3.18 (t, J=7.4 Hz), 3.22 (t, J=7.4 Hz), 2H], 4.41 (q, J=7.4 Hz, 2H), 7.48 (d, J=8.4 Hz, 1H), [7.83 (d, J=8.4 Hz), 7.85 (d, J=8.4 Hz), 1H] IR (neat, cm$^{-1}$): 1750, 1745, 1395, 1365, 1300, 1280, 1220, 1180, 1145

EXAMPLE 34
Production of N-methyl-N-propyl [3-(3-carbamoyl-2,6-dichlorophenyl)-1,2,5-thiadiazol-4-yl] carbamate (Compound 93)

In acetonitrile, a mixture of 80 mg of 3-(3-carbamoyl-2,6-dichlorophenyl)-4-hydroxy-1,2,5-thiadiazole, 41 mg of potassium carbonate, and 41 mg of N-methyl-N-propylcarbamoyl chloride was heated and refluxed for 12 hours. After spontaneous cooling, the reaction mixture was poured into dilute hydrochloric acid, and extracted with ether. The ether layer was washed with water, and saturated aqueous sodium chloride solution successively, dried over anhydrous magnesium sulfate, and concentrated. The concentrate was purified by silica gel column chromatography to obtain 41 mg of N-methyl-N-propyl [3-(3-carbamoyl-2,6-dichlorophenyl)-1,2,5-thiadiazol-4-yl] carbamate.

Oily matter $^1$H-NMR (Solvent: CDCl$_3$, Unit: δ ppm) 0.78 (t, J=7.3 Hz, 3H), 1.48 (sextet, J=7.3 Hz, 2H), [2.90 (s), 2.94 (s), 3H], [3.18 (t, J=7.3 Hz), 3.23 (t, J=7.3 Hz), 2H], [6.21 (bs), 6.31 (bs), 2H], 7.50 (d, J=8.4 Hz, 1H), [7.78 (d, J=8.4 Hz), 7.80 (d, J=8.4 Hz), 1H] IR (neat, cm$^{-1}$): 3450, 3330, 3200, 1735, 1670, 1400, 1360, 1225, 1150

The properties of a compound produced in the same manner as in Example 34 are shown in Example 35.

EXAMPLE 35
N-Methyl-N-propyl [3-(3-carboxy-2,6-dichlorophenyl)-1,2,5-thiadiazol-4-yl] carbamate (Compound 89)

Oily matter $^1$H-NMR (Solvent: CDCl$_3$, Unit: δ ppm): [0.66 (t, J=7.6 Hz), 0.71 (t, J=7.6 Hz), 3H], 1.2–1.5 (m, 2H), [2.69 (s), 2.83 (s), 3H], 2.9–3.2 (m, 2H), 7.26 (d, J=8.1 Hz, 1H), 7.5–7.7 (m, 1H) IR (neat, cm$^{-1}$): 3700–3100., 1740, 1600, 1400, 1390, 1360, 1230, 1150

EXAMPLE 36
Production of N-(2-carbamoylethyl)-N-methyl [3-(2,6-dichlorophenyl)-1,2,5-thiadiazol-4-yl] carbamate (Compound 223)

In 3 mL of ethanol, was dissolved 360 mg of N-(2-cyanoethyl)-N-methyl [3-(2,6-dichlorophenyl)-1,2,5-thiadiazol-4-yl] carbamate. Thereto, 6 mL of concentrated hydrochloric acid was added. The mixture was stirred at 30° C. for 2 hours. The reaction mixture was poured into water, and was extracted with diethyl ether. The diethyl ether layer was washed with dilute hydrochloric acid, and water successively, dried over anhydrous magnesium sulfate, and concentrated. The concentrate was purified by silica gel column chromatography to obtain 240 mg of N-(2-carbamoylethyl)-N-methyl [3-(2,6-dichlorophenyl)-1,2,5-thiadiazol-4-yl] carbamate.

Melting point: 160–161° C.

$^1$H-NMR (Solvent: CDCl$_3$, Unit: δ ppm) [2.40 (t, J=7.0 Hz), 2.44 (t, J=7.0 Hz), 2H], [2.95 (s), 3.00 (s), 3H], 3.52 (t, J=7.0 Hz), 3.59 (t, J=7.0 Hz), 2H], [5.43 (br s), 5.81 (br s), 2H], 7.3–7.5 (m, 3H) IR (KBr, cm$^{-1}$): 3440, 3300, 3200, 1735, 1680, 1620, 1455, 1430, 1380, 1305, 1230, 1190, 1130, 790, 780

EXAMPLE 37
Production of N-(2-carboxylethyl)-N-methyl [3-(2,6-dichlorophenyl)-1,2,5-thiadiazol-4-yl] carbamate (Compound 221)

To 360 mg of N-(2-cyanoethyl)-N-methyl [3-(2,6-dichlorophenyl)-1,2,5-thiadiazol-4-yl] carbamate, 10 mL of concentrated hydrochloric acid was added, and the mixture was stirred at 60° C. for 6 hours. The reaction mixture was poured into water, and was extracted with diethyl ether. The diethyl ether layer was washed with dilute hydrochloric acid, and water successively, dried over anhydrous magnesium sulfate, and concentrated. The concentrate was purified by silica gel column chromatography to obtain 280 mg of N-(2-carboxyethyl)-N-methyl [3-(2,6-dichlorophenyl)-1,2,5-thiadiazol-4-yl] carbamate.

Oily matter $^1$H-NMR (Solvent: CDCl$_3$, Unit: δ ppm) [2.52 (t, J=7.0 Hz), 2.53 (t, J=7.0 Hz), 2H], [2.96 (s), 3.01 (s), 3H], [3.49 (t, J=7.0 Hz), 3.58 (t, J=7.0 Hz), 2H], 7.3–7.5 (m, 3H), 9.4 (br s, 1H) IR (neat, cm$^{-1}$): 3600–2400, 1760–1700, 1430, 1380, 1230, 1190, 1120, 790

EXAMPLE 38
Production of N-[2-(ethoxycarbonyl)ethyl]-N-methyl [3-(2,6-dichlorophenyl)-1,2,5-thiadiazol-4-yl] carbamate (Compound 224)

In 5 mL of ethanol, was dissolved 200 mg of N-(2-carboxyethyl)-N-methyl [3-(2,6-dichlorophenyl)-1,2,5-thiadiazol-4-yl] carbamate. Thereto, 0.2 mL of concentrated hydrochloric acid was added. The mixture was stirred at 60° C. for 6 hours. The reaction mixture was poured into water, and was extracted with diethyl ether. The diethyl ether layer was washed with 10% sodium hydrogencarbonate solution, and water successively, dried over anhydrous magnesium sulfate, and concentrated. The concentrate was purified by silica gel column chromatography to obtain 180 mg of N-[2-(ethoxycarbonyl)ethyl]-N-methyl [3-(2,6-dichlorophenyl)-1,2,5-thiadiazol-4-yl] carbamate.

Oily matter $^1$H-NMR (Solvent: CDCl$_3$, Unit: δ ppm): 1.23 (t, J=7.0 Hz, 3H), [2.43 (t, J=7.0 Hz), 2.44 (t, J=7.0 Hz), 2H], [2.92 (s), 2.98 (s), 3H], [3.47 (t, J=7.0 Hz), 3.56 (t, J=7.0 Hz), 2H], 4.10 (q, J=7.0 Hz, 2H), 7.3–7.5 (m, 3H) IR (neat, cm$^{-1}$): 1760–1720, 1430, 1380, 1230, 1190, 1120, 790

EXAMPLE 39
Production of 3-(2-bromoethoxy)-4-(2,6-dichlorophenyl)-1,2,5-thiadiazole (Compound 160)

In acetonitrile, were mixed and stirred 0.49 g of 3-(2,6-dichlorophenyl)-4-hydroxy-1,2,5-thiadiazole, 0.3 g of potassium carbonate, and 1.9 g of 1,2-dibromoethane at 80° C. for one hour. After spontaneous cooling, the reaction mixture was poured into water, and was extracted with diethyl ether. The diethyl ether layer was washed with dilute hydrochloric acid, 10% sodium hydrogencarbonate, and water successively, dried over anhydrous magnesium sulfate, and concentrated. The concentrate was purified by silica gel chromatography to obtain 1.04 g of 3-(2-bromoethoxy)-4-(2,6-dichlorophenyl)-1,2,5-thiadiazole.
Melting point: 60–61° C.

$^1$H-NMR (Solvent: CDCl$_3$, Unit: δ ppm): 3.63 (t, J=6.5 Hz, 2H), 4.77 (t, J=6.5 Hz, 2H), 7.3–7.5 (m, 3H) IR (KBr, cm$^{-1}$): 1485, 1430, 1410, 1360, 1290, 1245, 790

EXAMPLE 40

Production of 3-(2,6-dichlorophenyl)-4-[2-(N-methyl-N-propylamino)ethoxy]-1,2,5-thiadiazole (Compound 161)

In dimethoxyethane, were mixed and stirred 0.35 g of 3-(2-bromoethoxy)-4-(2,6-dichlorophenyl)-1,2,5-thiadiazole, 0.3 g methylpropylamine at 50° C. for 6 hours. The reaction mixture was concentrated, and was purified by silica gel chromatography to obtain 0.2 g of 3-(2,6-dichlorophenyl)-4-[2-(N-methyl-N-propylamino)ethoxy]-1,2,5-thiadiazole.
Oily matter $^1$H-NMR (Solvent: CDCl$_3$, Unit: δ ppm) 0.81 (t, J=7.5 Hz, 3H), 1.41 (sextet, J=7.5 Hz, 3H), 2.25 (s, 3H), 2.32 (t, J=7.5 Hz, 2H), 2.76 (t, J=6.0 Hz, 2H), 4.53 (t, J=6.0 Hz, 2H), 7.2–7.45 (m, 3H) IR (neat, cm$^{-1}$): 3000–2700, 1520, 1490, 1430, 1245, 1025, 790

EXAMPLE 41

Virucidal test against HIV:

In RPMI1640 culture medium containing 20 mM HEPES buffer solution, 10% bovine fetus serum, and 20 μg/mL gentamycin, 3×10$^4$ cells of MT-4 (which will be killed by infection with HIV) were infected with HIV at a rate of 0.02 HIV per cell. To the fractions of the culture, predetermined portions of a sample containing the thiadiazole derivative of the compound No. shown in Table 27 and 28 were added, and the culture fractions were incubated at 37° C. After incubation for 5 days, living cells were measured by the MTT method to derive the compound concentration (EC$_{50}$) which is effective to protects 50% of the MT-4 cells from death by HIV. Separately, the MT-4 cells were incubated in the same manner without infection by HIV, and the compound concentration (CC$_{50}$) which causes death of 50% of the MT-4 cells. The ratio of CC$_{50}$/EC$_{50}$ is the selectivity index (S.I.). The results are shown in Tables 27 and 28.

TABLE 27

| Compound No. | EC$_{50}$ (μg/ml) | CC$_{50}$ (μg/ml) | S. I. |
|---|---|---|---|
| 21 | 0.15 | 36 | 240 |
| 22 | 0.021 | 22 | 1048 |
| 70 | 0.026 | 9.4 | 362 |
| 71 | 0.002 | 4.7 | 2350 |
| 87 | 0.003 | 23 | 7667 |
| 91 | 0.063 | 9.1 | 144 |
| 93 | 1.1 | 65 | 59 |
| 99 | 0.008 | 22 | 2750 |
| 127 | 1.5 | 31 | 21 |
| 128 | 0.19 | 9.2 | 48 |
| 130 | 0.014 | 14 | 1000 |
| 131 | 0.29 | 5.4 | 19 |
| 138 | 1.1 | 9.9 | 9 |
| 145 | 0.07 | 2.7 | 39 |
| 146 | 0.3 | 1.9 | 6 |
| 149 | 1.7 | 8.6 | 5 |
| 155 | 0.37 | >100 | >270 |
| 156 | 1.8 | 43 | 24 |
| 157 | 0.36 | 46 | 128 |
| 159 | 2.2 | 11 | 5 |
| 160 | 0.32 | 4.8 | 15 |
| 161 | 0.8 | 8.3 | 10 |
| 195 | 1.5 | 37 | 25 |

TABLE 28

| Compound No. | EC$_{50}$ (μg/ml) | CC$_{50}$ (μg/ml) | S. I. |
|---|---|---|---|
| 202 | 2.5 | 18 | 7 |
| 218 | 0.38 | 64 | 168 |
| 219 | 0.018 | 46 | 2556 |
| 220 | 3.5 | 63 | 18 |
| 222 | 1.4 | >100 | >71 |
| 223 | 2.6 | >100 | >38 |
| 224 | 0.13 | 50 | 385 |

Industrial applicability:

The arylthiadiazole derivative represented by General Formula [I] or [II] their salts exhibit viricidal effect, and is useful as a viricide.

What is claimed is:

1. An arylthiadiazole derivative represented by General Formula, or a salt thereof:

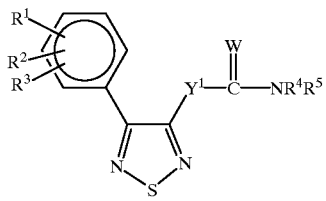

[I]

where

Y$^1$ is an oxygen atom or a sulfur atom;

W is an oxygen atom or a sulfur atom;

one of R$^1$, R$^2$, and R$^3$ is an amino group which may be substituted by one or two independent alkyls of 1–6 carbons;

a carboxyl group; a carbonyl group which is substituted by an alkoxyl of 1–4 carbons; a carbamoyl group which may be substituted by one or two independent alkyls of 1–6 carbons;

a cyano group; or an alkyl group of 1–6 carbons which is substituted by a hydroxyl, an alkoxyl of 1–4 carbons, an alkoxyl of 1–4 carbons (which is further substituted by another alkoxyl of 1–4 carbons), or a silyloxy (which is substituted by three independent alkyls of 1–6 carbons);

the other two of R$^1$, R$^2$, and R3 are independently a hydrogen atom; a halogen atom; an alkyl group of 1–6 carbons which may be substituted by a hydroxyl, an alkoxyl of 1–4 carbons, an alkoxyl of 1–4 carbons (which is further substituted by another alkoxyl of 1–4 carbons), or a silyloxy (which is substituted by three independent alkyls of 1–6 carbons; a trifluoromethyl group; an alkoxyl of 1–4 carbons; a carboxyl group; a carbonyl group which is substituted by an alkoxyl of 1–4 carbons; a carbamoyl group which may be substituted by one or two independent alkyls of 1–6 carbons;

a cyano group; a hydroxyl group; a hydroxymethyl group; a nitro group; or an amino group which may be substituted by one or two independent alkyls of 1–6 carbons;

R$^4$, and R$^5$ are independently a hydrogen atom, an alkoxyl group of 1–4 carbons, an alkyl group of 1–6 carbons which may be substituted by an alkoxyl of 1–4 carbons, a hydroxyl, a cyano, a carboxyl, a carbamoyl, a carbonyl (substituted by alkoxyl of 1–4 carbons), or a group of

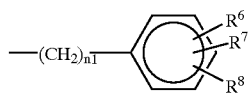

or $R^4$ and $R^5$ are linked together to form a group of

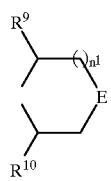

$R^6$, $R^7$, and $R^8$ are independently a hydrogen atom, a halogen atom, an alkyl group of 1–6 carbons, or an alkoxyl group of 1–4 carbons;

$R^9$, and $R^{10}$ are independently a hydrogen atom, or an alkyl group of 1–6 carbons;

E is a —CH$_2$— group, or an oxygen atom; and $n^1$ is an integer of 0 to 2.

2. An arylthiadiazole derivative represented by General Formula below, or a salt thereof:

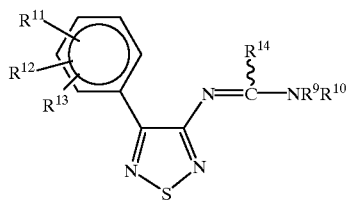

where $R^9$, and $R^{10}$ are independently a hydrogen atom, or an alkyl group of 1–6 carbons;

$R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

$R^{14}$ is a hydrogen atom, an alkyl group of 1–6 carbons, or a phenyl group (which may be substituted by a halogen, an alkyl of 1–6 carbons, or an alkoxyl of 1–4 carbons).

3. An arylthiadiazole derivative represented by General Formula below, or a salt thereof:

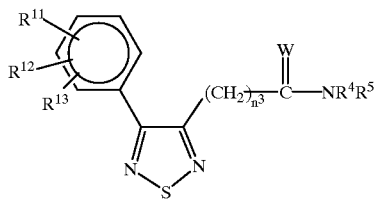

where $n^3$ is 0 or 1;

W is an oxygen atom or a sulfur atom;

$R^4$, and $R^5$ are independently a hydrogen atom, an alkoxyl group of 1–4 carbons, an alkyl group of 1–6 carbons which may be substituted by an alkoxyl of 1–4 carbons, a hydroxyl, a cyano, a carboxyl, a carbamoyl, a carbonyl substituted by alkoxyl of 1–4 carbons, or a group of

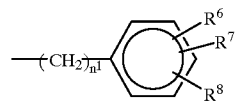

or $R^4$ and $R^5$ linked together to form a group of

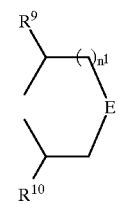

$R^6$, $R^7$, and $R^8$ are independently a hydrogen atom, a halogen atom, an alkyl group of 1–6 carbons, or an alkoxyl group of 1–4 carbons;

$R^9$, and $R^{10}$ are independently a hydrogen atom, or an alkyl group of 1–6 carbons;

E is a —CH$_2$— group, or an oxygen atom; and $n^1$ is an integer of 0 to 2; and $R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group.

4. An arylthiadiazole derivative represented by General Formula below, or a salt thereof:

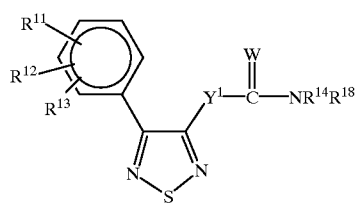

where $Y^1$ is an oxygen atom or a sulfur atom;

W is an oxygen atom or a sulfur atom;

$R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

$R^{14}$ is a hydrogen atom, an alkyl group of 1–6 carbons, or a phenyl group which may be substituted by a halogen, an alkyl of 1–6 carbons, or an alkoxyl of 1–4 carbons; and $R^{18}$ is an alkyl group of 1–6 carbons which is substituted by a hydroxyl, a cyano, a carboxyl, a carbamoyl, or a carbonyl substituted by an alkoxyl of 1–4 carbons.

5. An arylthiadiazole derivative represented by General Formula below, or a salt thereof:

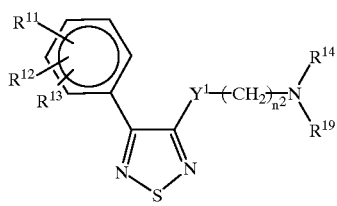

where $Y^1$ is an oxygen atom or a sulfur atom;

$n^2$ is 1 or 2;

$R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

$R^{14}$ is a hydrogen atom, an alkyl group of 1–6 carbons, or a phenyl group (which may be substituted by a halogen, an alkyl of 1–6 carbons, or an alkoxyl of 1–4 carbons); and $R^{19}$ is a hydrogen atom, or an alkyl group of 1–6 carbons which may be substituted by an alkoxyl of 1–4 carbons.

6. An arylthiadiazole derivative represented by General Formula below, or a salt thereof:

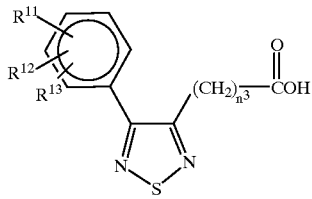

where $R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group; and $n^3$ is 0 or 1 provided that $R^{11}$, $R^{12}$, and $R^{13}$ are not simultaneously a hydrogen atom when $n^3$ is 0.

7. A virucidal composition, comprising a pharmaceutically acceptable carrier and an arylthiadiazole of General Formula or a salt thereof as an active ingredient:

[II]

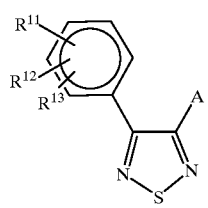

where $R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

A is a group of

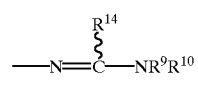

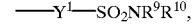

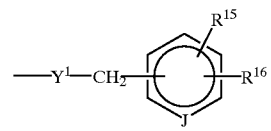

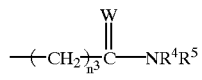

or

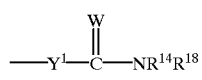

where $R^{14}$ is a hydrogen atom, an alkyl group of 1–6 carbons, or a phenyl group (which may be substituted by a halogen, an alkyl of 1–6 carbons, or an alkoxyl of 1–4 carbons);

$R^{15}$, and $R^{16}$ are independently a hydrogen atom, a halogen atom, an alkoxyl group of 1–4 carbons, a nitro group, or an alkyl group of 1–6 carbones which may be substituted with a halogen;

$R^{17}$ is a halogen atom, or $Y^2$—$R^{19}$;

$R^{18}$ is an alkyl group of 1–6 carbons which is substituted by a hydroxyl, a cyano, a carboxyl, a carbamoyl, or a carbonyl substituted by an alkoxyl of 1–4 carbons;

$R^{19}$ is a hydrogen atom, or an alkyl group which may be substituted by an alkoxyl of 1–4 carbons;

J is —CH=, or —N=;

$n^2$ is 1 or 2;

$n^3$ is 0 or 1;

$Y^2$ is an oxygen atom, a sulfur atom, or —$NR^{14}$—;

$R^4$, $R^5$, $R^9$, $R^{10}$, $R^{14}$, $Y^1$, and W are the same as defined above.

8. A virucidal composition, comprising a pharmaceutically acceptable carrier and a virucidally effective amount of the arylthiadiazole derivative of claim 1 or a salt thereof.

9. A virucidal composition, comprising a pharmaceutically acceptable carrier and a virucidally effective amount of an arylthiadiazole derivative of General Formula or a or a salt thereof:

[II]

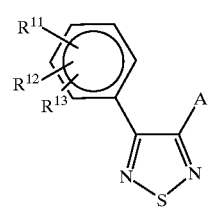

where $R^{11}$, $R^{12}$, and $R^{13}$ are independently a hydrogen atom, a halogen atom, an alkyl group of 1 to 6 carbons, a trifluoromethyl group, an alkoxyl group of 1–4 carbons, a hydroxyl group, or a nitro group;

A is

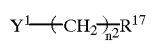

where $Y^1$ is an oxygen atom or a sulfur atom;

$n^2$ is 1 or 2;

$R^{17}$ is a halogen atom, or $Y^2$—$R^{19}$;

$Y^2$ is an oxygen atom, a sulfur atom, or —$NR^{14}$—;

$R^{14}$ is a hydrogen atom, an alkyl group of 1–6 carbons, or a phenyl group (which may be substituted by a halogen, an alkyl of 1–6 carbons, or an alkoxyl of 1–4 carbons); and $R^{19}$ is a hydrogen atom, or an alkyl group which may be substituted by an alkoxyl of 1–4 carbons.

* * * * *